US009808479B2

(12) United States Patent
Anton et al.

(10) Patent No.: US 9,808,479 B2
(45) Date of Patent: Nov. 7, 2017

(54) SIRNA AND THEIR USE IN METHODS AND COMPOSITIONS FOR THE TREATMENT AND / OR PREVENTION OF EYE CONDITIONS

(71) Applicant: Sylentis SAU, Madrid (ES)

(72) Inventors: Ana Isabel Jimenez Anton, Madrid (ES); Victoria Gonzalez Fajardo, Madrid (ES); Veronica Ruz Palomar, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 14/425,459

(22) PCT Filed: Sep. 4, 2013

(86) PCT No.: PCT/EP2013/068245
§ 371 (c)(1),
(2) Date: Mar. 3, 2015

(87) PCT Pub. No.: WO2014/037377
PCT Pub. Date: Mar. 13, 2014

(65) Prior Publication Data
US 2015/0224131 A1    Aug. 13, 2015

(30) Foreign Application Priority Data
Sep. 5, 2012  (GB) .................................. 1215857.2

(51) Int. Cl.
*A61K 48/00* (2006.01)
*C12N 15/11* (2006.01)
(Continued)

(52) U.S. Cl.
CPC ....... *A61K 31/7088* (2013.01); *C12N 15/1138* (2013.01); *C12N 2310/14* (2013.01); *C12N 2310/321* (2013.01)

(58) Field of Classification Search
USPC ........................................... 514/44; 536/24.5
See application file for complete search history.

(56) References Cited

U.S. PATENT DOCUMENTS

| 4,343,794 A | 8/1982 | Podos et al. |
| 4,617,299 A | 10/1986 | Knepper |

(Continued)

FOREIGN PATENT DOCUMENTS

| EP | 1 527 176 | 1/2007 |
| GB | 2406568 | 4/2005 |

(Continued)

OTHER PUBLICATIONS

Gonzalez Victoria et al., "SYL1001 Targeting TRPV1 Receptor for the Treatment of Ocular Pain Associated to Dry Eye Syndrome," Database Biosis, Accession No. PREV201200523107, May 3, 2011, Poster/Presentation Abstract #3844/D977, Presented at the Association for Research in Vision and Ophthalmology, Inc. (ARVO).

(Continued)

*Primary Examiner* — Terra C Gibbs
(74) *Attorney, Agent, or Firm* — Margaret B. Brivanlou; King & Spalding LLP

(57) ABSTRACT

The invention relates to methods and compositions for the treatment and/or prevention of eye conditions related to high levels of expression and/or activity of the vanilloid-1 receptor (TRPV).

14 Claims, 4 Drawing Sheets

(51) Int. Cl.
 C07H 21/02 (2006.01)
 C07H 21/04 (2006.01)
 A61K 31/7088 (2006.01)
 C12N 15/113 (2010.01)

(56) References Cited

U.S. PATENT DOCUMENTS

| | | | |
|---|---|---|---|
| 4,652,586 | A | 3/1987 | Nathanson |
| 4,757,089 | A | 7/1988 | Epstein |
| 4,812,448 | A | 3/1989 | Knepper |
| 5,075,323 | A | 12/1991 | Fain et al. |
| 5,242,943 | A | 9/1993 | Louis et al. |
| 5,260,059 | A | 11/1993 | Acott et al. |
| 5,464,866 | A | 11/1995 | Clark et al. |
| 5,545,626 | A | 8/1996 | Stein et al. |
| 5,585,401 | A | 12/1996 | Brandt et al. |
| 6,365,576 | B1 | 4/2002 | Carr |
| 6,372,249 | B1 | 4/2002 | Smith et al. |
| 6,489,307 | B1 | 12/2002 | Phillips et al. |
| 7,176,304 | B2 | 2/2007 | McSwiggen et al. |
| 7,294,504 | B1 | 11/2007 | Wang |
| 7,462,602 | B2 | 12/2008 | Schultz et al. |
| 7,521,431 | B2 | 4/2009 | Reich et al. |
| 7,579,457 | B2 | 8/2009 | Khvorova et al. |
| 7,592,324 | B2 | 9/2009 | Shepard et al. |
| 7,592,325 | B2 | 9/2009 | Jimenez et al. |
| 7,618,814 | B2 | 11/2009 | Bentwich |
| 7,655,789 | B2 | 2/2010 | Khvorova et al. |
| 7,687,665 | B2 | 3/2010 | Yao et al. |
| 7,691,997 | B2 | 4/2010 | Khvorova et al. |
| 7,700,575 | B2 | 4/2010 | Andrew et al. |
| 8,090,542 | B2 | 1/2012 | Khvorova et al. |
| 8,354,385 | B2 | 1/2013 | Boj et al. |
| 2002/0055536 | A1 | 5/2002 | DeWitte et al. |
| 2002/0114784 | A1 | 8/2002 | Li et al. |
| 2002/0165158 | A1 | 11/2002 | King |
| 2004/0029275 | A1 | 2/2004 | Brown et al. |
| 2004/0115641 | A1 | 6/2004 | Cowsert et al. |
| 2004/0167090 | A1 | 8/2004 | Monahan et al. |
| 2004/0198640 | A1 | 10/2004 | Leake et al. |
| 2004/0209832 | A1 | 10/2004 | McSwiggen et al. |
| 2004/0224405 | A1 | 11/2004 | Leake et al. |
| 2004/0235031 | A1 | 11/2004 | Schultz et al. |
| 2004/0259247 | A1 | 12/2004 | Tuschl et al. |
| 2004/0266707 | A1 | 12/2004 | Leake et al. |
| 2005/0020521 | A1 | 1/2005 | Rana |
| 2005/0165049 | A1 | 7/2005 | Hulme et al. |
| 2005/0171039 | A1 | 8/2005 | McSwiggen et al. |
| 2005/0208658 | A1 | 9/2005 | Castonguay |
| 2005/0255487 | A1 | 11/2005 | Khvorova et al. |
| 2006/0058266 | A1 | 3/2006 | Manoharan et al. |
| 2006/0094032 | A1 | 5/2006 | Fougerolles et al. |
| 2006/0122136 | A1 | 6/2006 | Schubert et al. |
| 2006/0172963 | A1 | 8/2006 | Shepard et al. |
| 2006/0172965 | A1 | 8/2006 | Shepard et al. |
| 2006/0257851 | A1 | 11/2006 | Bentwich |
| 2007/0049543 | A1 | 3/2007 | McSwiggen et al. |
| 2007/0093435 | A1 | 4/2007 | Andrews et al. |
| 2007/0167384 | A1 | 7/2007 | Leake et al. |
| 2008/0085998 | A1 | 4/2008 | Khvorova et al. |
| 2009/0326044 | A1 | 12/2009 | Shepard et al. |
| 2010/0286230 | A1 | 11/2010 | Acosta Boj et al. |

FOREIGN PATENT DOCUMENTS

| | | |
|---|---|---|
| GB | 2406856 | 4/2005 |
| WO | WO 03/057840 | 7/2003 |
| WO | WO 03/059267 | 7/2003 |
| WO | WO 03/070744 | 8/2003 |
| WO | WO 03/087367 | 10/2003 |
| WO | WO 2004/009794 | 1/2004 |
| WO | WO 2004/009796 | 1/2004 |
| WO | WO 2004/029212 | 4/2004 |
| WO | WO 2004/042024 | 5/2004 |
| WO | WO 2004/042046 | 5/2004 |
| WO | WO 2005/032493 | 4/2005 |
| WO | WO 2005/040106 | 5/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/083945 | 8/2006 |
| WO | WO 2006/084217 | 8/2006 |
| WO | WO 2006/099353 | 9/2006 |
| WO | WO 2007/045930 | 4/2007 |
| WO | WO 2008/024983 * | 8/2007 |
| WO | WO 2009/023025 | 2/2009 |
| WO | WO 2009/067438 | 5/2009 |
| WO | WO 2011/148193 | 12/2011 |

OTHER PUBLICATIONS

Sylentis SAU, Notification of Transmittal of the International Search Report and the Written Opinion of the International Search Authority, or the Declaration, 6 pages, dated Dec. 6, 2013.

Abrams et al., "Comparison of Three Tonometers for Measuring Intraocular Pressure in Rabbits," Invest Ophthalmol Vis Sci. Apr. 1996, 37(5):940-944.

Achenbach et al., Oligonucleotide-Based Knockdown Technologies: Antisense Versus RNA Interference, ChemBioChem., 4, pp. 928-935, 2003.

Ahern et al., "Extracellular cations sensitize and gate capsaicin receptor TRPV1 modulating pain signaling", J. Neurosci. May 25, 2005;25(21):5109-16.

Akashi et al., "Suppression of Gene Expression by RNA Interference in Cultured Plant Cells," Antisense Nucleic Acid Drug Dev, 2001, 11(6):359-367.

Amaratunga et al., "Inhibition of Kinesin Synthesis and Rapid Anterograde Axonal Transport in Vivo by an Antisense Oligonucleotide," the Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191 , Apr. 2000.

Ambion, "The Basics: RNase Control," printout from website <<http://web.archive.org/web/20041207234247>>, dated 2004, retrieved on Sep. 17, 2009.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.

Banan et al., "The Ins and Outs of RNAi in Mammalian Cells," Current Pharmaceutical Biotechnology, 5, pp. 441-450, 2004.

Banerjee et al., "Control of Developmental Timing by Small Temporal RNAs: a Paradigm for RNA-mediated Regulation of Gene Expression," Bioessays, 2002, 24(2):119-129.

Barar J. et al., "Ocular novel drug delivery impacts of membranes and barriers," *Expert Opin. Drug Deliv.*, 5(5): 567-81, 2008.

Bass, "The Short Answer," Nature, vol. 411, pp. 428-429, 2001.

Basu et al., "Immunological role of neuronal receptor vanilloid receptor 1 expressed on dendritic cells", Proc Natl Acad Sci U S A. Apr. 5, 2005;102(14):5120-5. Epub Mar. 25, 2005.

Baumann et al., "Extracellular protons both increase the activity and reduce the conductance of capsaicin-gated channels", J Neurosci. 2000;20:RC80.

Bhattacharya et al., "Cochlin Deposits in the Trabecular Meshwork of the Glaucomatous DBA/2J mouse," Exp Eye Res., May 2005 80(5):741-744.

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec 3. 2004.

Bill, "Movement of Albumin and Dextran," Arch. Opthal., vol. 74, pp. 248-252, Aug. 1965.

Borrás, "Gene Expression in the Trabecular Meshwork and the Influence of Intraocular Pressure," *Progress in Retinal and Eye Research*, 22, 435-463, 2003.

(56) References Cited

OTHER PUBLICATIONS

Bodo et al., "A hot new twist to hair biology: involvement of vanilloid receptor-1 (VR1 !TRPV1) signaling in human hair growth control", Am J Pathol. Apr. 2005;166(4):985-98.
Bosher et al., "RNA Interference: Genetic Wand and Genetic Watchdog." Nat Cell Biol, 2000, 2(2):E31-6.
Braasch et al., "Novel Antisense and Peptide Nucleic Acid Strategies for Controlling Gene Expression," Biochemistry, 2002, 41(14):4503-4510.
Brock et al., "Tetrodotoxin-resistant impulses in single nociceptor nerve terminals in guinea-pig cornea",. J Physiol. Oct. 1, 1998;512 ( Pt 1):211-7.
Brock et al., "Effects of Ca2+ and K+ channel blockers on nerve impulses recorded from postganglionic sympathetic nerve terminals", the Journal of Physiology, 1995, 489, 389-402.
Brummelkamp et al., "A System for Stable Expression of Short Interfering RNAs in Mammalian Cells," Science, American Association for the Advancement of Science, 2002, 296(5567):550-553.
Busch et al., "Adenylyl Cyclase in Human and Bovine Trabecular Meshwork," Investigative Ophthalmology & Visual Science, 34(10), pp. 3028-3034, Sep. 1993.
Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.
Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.
Caplen et al., "Specific inhibition of Gene Expression by Small Double Stranded RNAs in Invertebrate and Vertebrate Systems," Proc. Natl. Acad. Sci. USA, 2001,98: 9742-9747.
Caterina et al., The vanilloid receptor: a molecular gateway to the pain pathway, Annu Rev Neurosci., 2001; 24:487-517.
Cho et al., "Small Interfering RNA-Induced TLR3 Activation Inhibits Blood and Lymphatic Vessel Growth," PNAS, pp. 1-6, Dec. 5, 2008.
Christoph et al., "Silencing of vanilloid receptor TRPV1 by RNAi reduces neuropathic and visceral pain in vivo", Biochemical and Biophysical Research Communications, 2006, vol. 350, pp. 238-243.
Comes N. and Borrás T, "Functional delivery of synthetic naked siRNA to the human trabecular meshwork in perfused organ cultures," Molec. Vision, 13: 1363-74, 2007.
Costagliola et al., "Effect of Oral Losartan Potassium Administration on Intraocular Pressure in Normotensive and Glaucomatous Human Subjects," Exp Eye Res., Aug. 2000, 71(2):167-171.
Costagliola et al., "Effect of Oral Captopril (SQ 14225) on Intraocular Pressure in Man," Eur. J. Opthalmol, Jan. 1995, 5(1):19-25.
Crooke et al., "Nucleotides in Ocular Secretions: Their Role in Ocular Physiology," Pharmacology & Therapeutics, 119, pp. 55-73, 2008.
Cullinane et al., "Renin-angiotensin System Expression and Secretory Function in Cultured human Ciliary Cody Nonpigmented Epithelium," Br J Ophthalmol. Jun. 2002, 86(6):6766-83.
Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.
Di Marzo et al., "Endovanilloid signaling in pain", Curr Opin Neurobiol., Aug. 2002;12(4):372-9.
Diffen, DNA vs. RNA—Difference and Comparison, retrieved from <<http://www.diffen.com/difference/Dna_vs_Rna>> on May 21, 2009.
Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.
Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in *Drosophila melanogaster* Embryo Lysate," EMBO Journal, vol. 20, No. 23, pp. 6877-6888, 2001.
Elbashir et al., "RNA Interference is Mediated by 21- and 22-Nucleotide RNAs," Genes Dev, 2001, 15(2):188-200.
Elbashir et al., "Analysis of Gene Function in Somatic Mammalian Cells Using Small Interfering RNAs," Methods, 26, pp. 199-213, 2002.
Elena et al., "Autoradiographic Localization of Beta-Adrenergic Receptors in Rabbit Eye," Investigative Ophthalmology & Visual Science, 28, pp. 1436-1441, Aug. 1987.
Epstein et al., "*Effect of Iodoacetamide Perfusion on Outflow Facility and Metabolism of the Trabecular Meshwork,*" Invest. Ophthalmol. Vis. Sci., 625-631, May 1981.
Fattal et al., "Ocular Delivery of Nucleic Acids: Antisense Oligonucleotides, Aptamers and siRNA," Advanced Drug Delivery Reviews, 2006, 58:1203-1223.
Fire et al., "Potent and Specific Genetic Interference by Double Stranded RNA in a Caenorhabditis Elegans," Nature, 1998, 391(6669):806-11.
Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.
Garcia-Martinez et al., "Attenuation of thermal nociception and hyperalgesia by VR1 blockers", Proc Natl Acad Sci U S A. Feb. 19, 2002;99(4):2374-9.
Gawa et al., The Journal of Pharmacology and Experimental Therapeutics, 313(1), pp. 474-484, 2005.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.
Gil et al., "Induction of Apoptosis by the dsRNA-dependent Protein Kinase (PKR): Mechanism of Action," Apoptosis, 2000, 5(2):107-114.
Gonzalez et al., "Genes Upregulated in the Human Trabecular Meshwork in Response to Elevated Intraocular Pressure," Investigative Opthalmology & Visual Science, Feb. 2000, 41(2):352-361.
Grant et al., "Insulin-like growth factors in vitreous. Studies in control and diabetic subjects with neovascularization", Diabetes, 1986; 35:416-420.
Grosshans et al., "Micro-RNAs: Small is Plentiful," J Cell Bioi, 2002, 156(1):17-21.
Grunweller et al., "Comparison of Different Antisense Strategies in Mammalian Cells Using Locked Nucleic Acids, 2'O-methyl RNA," Nucleic Acids Research, vol. 31, No. 12, pp. 3185-3193, Jun. 15, 2003.
Grueneweller et al, "RNA Interference Approaches for Target Validation in Pain Research", Society for Neurochemistry, Journal of Neurochemistry, 2005, vol. 94 (Suppl. 2), pp. 141.
Hammond et al., "Post-Transcriptional Gene Silencing by Double-Standed RNA," Nature, 2001, 2:110-119.
Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.
Herkel et al., "Update on Topical Carbonic Anhydrase Inhibitors," Current Opinion in Ophthamology, Apr. 2001, 12(2):88-93.
Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.
Horinouchi et al., "Pharmacological Evaluation of Ocular β-Adrenoceptors in Rabbit by Tissue Segment Binding Method," Life Sciences, 84, pp. 181-187, 2009.
Inokuchi et al., "Vitreous levels of insulin-like growth factor-I in patients with proliferative diabetic retinopathy", Curr. Eye Res., 2001; 23:368-371.
Jens Kurreck, "Antisense Technologies," Eur. J. Biochem., 270, pp. 1628-1644, 2003.

(56) References Cited

OTHER PUBLICATIONS

Jens Kurreck, "Antisense and RNA Interference Approaches to Target Validation in Pain Research," Current Opinion in Drug Discovery & Development, 7(2), pp. 179-187, 2004.
Jia et al., "TRPV1 receptor: a target for the treatment of pain, cough, airway disease and urinary incontinence", Drug News Perspect. Apr. 2005;18{3):165-71.
Kaplan et al., "Aqueous Humor Flow in Unilateral Carotid Stenosis," Journal of Glaucoma, 5, pp. 237-240, 1996.
Khaw et al., "Glaucoma-1: Diagnosis," BMJ, 2004a, 328:97-99.
Khaw et al., "Glaucoma-2: Treatment," BMJ, 2004, 328:156-158.
Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.
Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.
Krutzfeldt et al., "Silencing of microRNAs in vivo with 'Antagomirs'," Nature, 2005, 438(7068):685-689.
Kwon et al., "Primary Open-Angle Glaucoma," the New England Journal of Medicine, 360(11), pp. 1113-1124, Mar. 12, 2009.
Lilja et al., "Development of a sensory neuronal cell model for the estimation of mild eye irritation", Altern Lab Anim. Oct. 2004;32(4):339-43.
Lograno et al., "Receptor-Responses in Fresh Human Ciliary Muscle," Br. J. Pharmac., 87, pp. 379-385, 1986.
Madsen, "Ocular Finding in 123 Patients with Proliferative Diabetic Retinopathy," Documenta Ophthalmologica, Advances in ophthalmology, May 14, 1971, 29(2):345-349.
Mahato et al., "Modulation of Gene Expression by Antisense and Antigene Oligodeoxynucleotides and Small Interfering RNA," Expert Opinion on Drug Delivery, Jan. 2005, 2(1):3-28.
Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.
Merimee et al., "Insulin-like growth factors. Studies in diabetics with and without retinopathy", N. Engl. J. Med., 1983; 309:527-530.
Meyer-Schwickerath et al., "Vitreous levels of the insulin-like growth factors I and II, and the insulin-like growth factor binding proteins 2 and 3, increase in neovascular eye disease—Studies in nondiabetic and diabetic subjects", J Clin Invest., 1993;92(6):2620-5.
Miller et al., "Allele-specific Silencing of Dominant Disease Genes," Proceedings of the National Academy of Sciences of USA, Jun. 10, 2003, 100(12):7195-7200.
Moriyama et al, "Sensitization of TRPV1 by EP1 and IP reveals peripheral nociceptive mechanism of prostaglandins", Mol Pain_ Jan. 17, 2005;1(1):3.
Muratovska et al., "Conjugate for Efficient Delivery of Short Interfering RNA (siRNA) into Mammalian Cells," FEBS Letters, 558, pp. 63-68, 2004.
Okabe et al., "Effect of Benzalkonium Chloride on Transscleral Drug Delivery," Investigative Ophthalmology & Visual Science, vol. 46, No. 2, pp. 703-708, Feb. 2005.
Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.
Osborne et al., "Some Current Ideas on the Pathogenesis and the Role of Neuroprotection in Glaucomatous Optic Neuropathy," Eur J Ophthalmol., Apr. 2003, 13Suppl. 3:S19-26.
Paddison et al., "Short hairpin RNAs (shRNAs) Induce Sequence-Specific Silencing in Mammalian Cells," Genes Dev, 2002, 16(8):948-958.

Pintor et al., "Adenosine Tetraphosphate, $Ap_4$, a Physiological Regulator of Intraocular Pressure in Normotensive Rabbit Eyes," the Journal of Pharmacology and Experimental Therapeutics, vol. 308, No. 2, pp. 468-473, 2004.
Rao et al., "Modulation of Aqueous Humor Outflow Facility by the Rho Kinase-Specific Inhibitor Y-27632," Investigative Opthalmology & Visual Science, Apr. 2001, 42(5): 1029-1037.
Reich et al., "Small Interfering RNA (siRNA) Targeting *VEGF* effectively Inhibits Ocular Neovascularization in a Mouse Model," Molecular Vision, 2003, 9:210-216.
Ruberte et al, "Increased ocular levels of IGF-1 in transgenic mice lead to diabetes-like eye disease", J Clin Invest Apr. 2004;113(8):1149-57.
Sakaguchi et al., "Chymase and Angiotensin Converting Enzyme Activities in a Hamster Model of Glaucoma Filtering Surgery," Curr Eye Res., May 2002, 24(5):325-331.
Schubert et al, "Local RNA Target Structure Influences siRNA Efficacy: Systematic Analysis of Intentionally Designed Binding Regions", J_ MoL Biol., 2006, 348, pp. 883-893.
Scherer et al., "Approaches for the Sequence-Specific Knockdown of mRNA," Nat. Biotechnology, 2003, 21(12):1457-1465.
Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.
Stamer et al., "Isolation and Culture of Human Trabecular Meshwork Cells by Extracellular Matrix Digestion," Current Eye Research, pp. 611-617, Jan. 10, 1995.
Stander et al, "Expression of vanilloid receptor subtype 1 in cutaneous sensory nerve fibers, mast cells, and epithelial cells of appendage structures", Exp DermatoL Mar. 2004;13(3):129-39.
Tan et al., "Recent Developments in Understanding the Pathophysiology of Elevated Intraocular Pressure," Current Opinion in Opthalmology, vol. 17, pp. 168-174, 2006.
Tuschl et al., "Targeted mRNA degradation by double-stranded RNA in vitro," Genes Dev., 1999, 13(24):3191-3197.
Uprichard et al., The Therapeutic Potential of RNA Interference, FEBS Letters, Oct. 31, 2005 579(26):5996-6007.
U. Herkel et al, Update on topical carbonic anhydrase inhibitors, Curr. Opthalmol., vol. 12 (2), p. 88-93, Apr. 2001, XP002375306.
Valls et al., "Validation of a Device for Transcorneal Drug Permeation Measure," Journal of Pharmaceutical and Biomedical Analysis, 48, pp. 657-663, 2008.
Van Buren et al, "Sensitization and translocation ofTRPV1 by insulin and IGF-1", Mol Pain, Apr. 27, 2005;1(1):17.
Vittal et al., "Changes in Gene Expression by Trabecular Meshword Cells in Response to Mechanical Stretching," Investigative Opthalmology & Visual Science, Aug. 2005, 46(8):2857-2868.
Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan. 4, 2005.
Wax et al., "Vacuolar $H^+$—ATPase in Ocular Ciliary Epithelium," Proc. Natl. Acad. Sci., vol. 94, pp. 6752-6757, Jun. 1997.
Wetering et al., "Specific Inhibition of Gene Expression Using a Stably Integrated, Inducible Small-Interfering-RNA Vector," EMBO Reports, Jun. 2003, 4(6):609-615.
Wianny et al., "Specific Interference with Gene Function by Double-Stranded RNA in Early Mouse Development," Nat Cell Biol, 2000, 2(2):70-75.
Williams BR, "Role of the Double-Stranded RNA-activated Protein kinase (PKR) in Cell Regulation," Biochem Soc Trans, 1997, 25(2):509-513.
Wirtz et al., "The Genetic Loci of Open-Angle Glaucoma," Ophthalmol. Clin. North Am. 2003 16:505-514.
Wiznerowicz et al., "Conditional Suppression of Cellular Genes: Lentivirus Vector-Mediated Drug-Inducible RNA Interference," Journal of Virology, Aug. 2003, 77(16):8957-8961.
Woodward et al., "The Inflow and Outflow of Anti-Glaucoma Drugs," Trends in Pharmacological Sciences, May 2004, 25(5):238-241.
Xie et al., "Harnessing in vivo siRNA Delivery for Drug Discovery and Therapeutic Development," Drug Discovery Today, Jan. 2006, 11(1-2):67-73.

(56) References Cited

OTHER PUBLICATIONS

Yang-Feng et al., " Chromosomal Organization of Adrenergic Receptor Genes," PNAS, 1990, 87:1516-1520.
Yang et al., "Early Growth Response Gene 1 Modulates Androgen Receptor Signaling in Prostate Carcinoma Cells," the Journal of Biological Chemistry, 278(41), pp. 39906-39911, 2003.
Office Action dated Jul. 14, 2008 in corresponding U.S. Appl. No. 11/360,305.
Office Action dated Jan. 29, 2009 in corresponding U.S. Appl. No. 11/360,305.
Office Action dated Nov. 12, 2008 in corresponding U.S. Appl. No. 11/574,169.
Final Office Action dated May 8, 2009 in corresponding U.S. Appl. No. 11/574,169.
Office Action dated Nov. 3, 2009 in corresponding U.S. Appl. No. 12/170,078.
Office Action dated Oct. 15, 2009 in corresponding U.S. Appl. No. 12/170,104.
Office Action dated Oct. 15, 2009 in corresponding U.S. Appl. No. 12/170,157.
Office Action dated Oct. 30, 2009 in corresponding U.S. Appl. No. 12/170,116.
Office Action dated Oct. 30, 2009 in corresponding U.S. Appl. No. 12/170,132.
Office Action dated Oct. 19, 2009 in corresponding U.S. Appl. No. 12/170,148.
Office Action dated Dec. 4, 2009 in corresponding U.S. Appl. No. 11/574,169.
Office Action dated Mar. 19, 2010 in corresponding U.S. Appl. No. 12/170,078.
Office Action dated Mar. 22, 2010 in corresponding U.S. Appl. No. 12/170,104.
Office Action dated Mar. 19, 2010 in corresponding U.S. Appl. No. 12/170,116.
Office Action dated Mar. 22, 2010 in corresponding U.S. Appl. No. 12/170,132.
Office Action dated Mar. 22, 2010 in corresponding U.S. Appl. No. 12/170,148.
Office Action dated Mar. 22, 2010 in corresponding U.S. Appl. No. 12/170,157.
Office Action dated Mar. 25, 2010 in corresponding U.S. Appl. No. 12/563,530.
Final Office Action dated Jul. 22, 2010 in corresponding U.S. Appl. No. 11/574,169.
Office Action dated Sep. 7, 2010 in corresponding U.S. Appl. No. 11/574,169.
Office Action dated Sep. 23, 2010 in corresponding U.S. Appl. No. 12/170,078.
Office Action dated Sep. 23, 2010 in corresponding U.S. Appl. No. 12/170,104.
Office Action dated Sep. 23, 2010 in corresponding U.S. Appl. No. 12/170,116.
Office Action dated Sep. 23, 2010 in corresponding U.S. Appl. No. 12/170,132.
Office Action dated Sep. 23, 2010 in corresponding U.S. Appl. No. 12/170,148.
Office Action dated Sep. 23, 2010 in corresponding U.S. Appl. No. 12/170,157.
Andrieu-Soler C., et al "Ocular gene therapy: A review of nonviral strategies," *Molecular Vision*, 12:1334-47, 2006.
Byrne et al., J. Ocular Pharmacology and Therapeutics, 29, pp. 855-864, 2013.
Bujalska et al., "Hexose-6-phosphate Dehydrogenase Confers Oxo-Reductase Activity Upon 11beta-hydroxysteroid Dehydrogenase Type 1," Journal of Molecular Endocrinology, 34(3), pp. 675-684, Jun. 2005.
Czauderna et al., "Structural Variations and Stabilising Modifications of Synthetic siRNAs in Mammalian Cells," Nucleic Acids Research, vol. 31, No. 11, pp. 2705-2716, Jun. 1, 2003.

Dejneka NS., et al., "Ocular Biodistribution of Bevasiranib Following a Single Intravitreal Injection to Rabbit Eyes," *Molecular Vision*, 14:997-1005, 2008.
Dos Santos ALG., et al "Intraocular Delivery of Oligonucleotides," *Current Pharmaceutical Biotechnology*, 6:7-15, 2005.
Doench et al., "Specificity of microRNA Target Selection in Translational Repression," Genes Dev., 18:504-511, 2004.
Davson H, "The Aqueous Humour and the Intraocular Pressure," Davson's Physiology of the Eye, $5^{th}$ edition, Pergamon Press, pp. 3-95, 1990.
Fattal et al., "Antisense Oligonucleotides, Aptamers and siRNA: Promises for the Treatment of Ocular Disease," Arch. Soc. Esp. Oftalmol, 8(1), pp. 1-4, 2006.
Flynn, "Efficient delivery of small interfering RNA for inhibition of IL-12p40 expression in vivo," J Inflamm (Lond), Oct. 1, 2004;1(1):4.
Gavva et al., J. of Pharmacology & Experimental Therapeutics, 313, pp. 474-484, 2005.
Ghate et al., "Barriers to Glaucoma Drug Delivery," J. Glaucoma, 17(2), pp. 147-156, Mar. 2008.
Gonzalez et al., "Reduction of Capsaicin-Induced Ocular Pain and Neurogenic Inflammation by Calcium Antagonists," Investigative Ophthalmology & Visual Science, 34(12), pp. 3329-3335, Nov. 1993.
Gonzalez et al., "A New Treatment for Ocular Pain Associated to Dry Eye Syndrome Based on RNAi Technology: In Vivo Results," Invest. Ophthalmol. Vis. Sci., E-Abstract and Poster 4676, 2009, 3 pages.
Jiménez et al., "Efficacy of Topically Administered siRNAs in Glaucoma Treatment: In vivo Results in Hypertensive Model," Investigative Ophthalmology & Visual Science, 50, E-Abstract 4054, 2009.
Jiménez et al., "$Na^+/K^+$ ATPase: A New Target for Treating Ocular Hypertension by RNAi," Investigative Ophthalmology & Visual Science, 48, E-Abstract 4809 2007.
Jiménez et al., "SYL04003: A New Therapeutic Candidate for Treating Ocular Hypertension using RNAi Technology," Investigative Ophthalmology & Visual Science, 49, E-Abstract 1643, 2008.
Jiménez et al., "SYL040012 a New siRNA-Based Treatment for Glaucoma: Pharmacokinetics and Mechanism of Action," Investigative Ophthalmology & Visual Science, 51, E-Abstract 176, 2010.
Liao et al., "Expression of Cell Surface Transmembrane Carbonic Anhydrase Genes CA9 and CA12 in the Human Eye: Overexpression of CA12 (CAXII) in Glaucoma," J. Med. Genet., 40:257-262, 2003.
Luna et al., "TRPV1 siRNA Topical Treatment Reduces the Response to Ocular Surface Irritation with Capsaicin," Invest. Ophthalmol. Vis. Sci., 48, E-Abstract and Poster, 373, 2007, 3 pages.
Hart WM, "Intraocular Pressure," Chapter 8, Adler's Physiology of the Eye: Clinical Application, Mosby-Year Book Inc., $9^{th}$ edition, pp. 248-267, 1992.
Mirshahi et al., "The Mineralocorticoid Hormone Receptor and Action in the Eye," Biochem Biophys Res Commun, vol. 219, pp. 150-156, 1996.
Nie et al., "The Potential Therapeutic of siRNA Eye Drops in Ocular Diseases," Bioscience Hypotheses, 2, pp. 223-225, 2009.
Papers filed on Mar. 2, 2012, from opponents in Opposition by Alcon Research, Ltd. against Australian Patent Application No. 2005276245 in the name of Sylentis SAU.
Peral et al., "Effect of Several siRNA in the Treatment of Ocular Hypertension and Glaucoma," Invest. Ophthalmol. Vis. Sci., 48, E-Abstract 4808, 2007.
Pintor et al., "SiRNA in the Treatment of Ocular Hypertension Targeting Alpha and Beta Adrenoceptors," Invest. Ophthalmol. Vis. Sci., 47, E-Abstract 403, 2006.
Rauz et al., "Expression and Putative Role of 11beta-Hydroxysteriod Dehydrogenase Isozymes Within the Human Eye," Investigative Ophthalmology & Visual Science, 42(9), pp. 2037-2042, 2001.
Rauz et al., "Inhibition of 11beta-hydroxysteriod dehydrogenase type 1 Lowers Intraocular Pressure in Patients with Ocular Hypertension," 96(7), pp. 481-490, Jul. 2003.

(56) References Cited

OTHER PUBLICATIONS

Ruz et al., "Phase I Study With a New siRNA: SYL040012. Tolerance and Effect on Intraocular Pressure," Investigative Ophthalmology Visual Science, 52, E-Abstract 223, 2011.

Stokes et al., "Distribution of Glucocorticoid and Mineralocorticoid Receptors and 11 β-Hydroxysteroid Dehydrogenases in Human and Rat Ocular Tissues," Invest. Ophthalmol. Vis Sci., 41(7), pp. 1629-1638, Jun. 2000.

Studies conducted in the Biochemistry Department of the School of Optics at the Universidad Complutense de Madrid, as filed in the Information Disclosure Statement of Oct. 30, 2008 (in U.S. Appl. No. 11/574,169).

Supuran et al., "Carbonic Anhydrase Inhibitors," Medicinal Research Reviews, 23(2):146-189, 2003.

Suzuki et al., "'Immunohistochemical Distribution of 11β-hydroxysteroid Dehydrogenase in Human Eye, " Mol Cell Endocrinol, vol. 173, pp. 121-125, 2001.

Tomlinson, "11Beta-hydroxsteroid Dehydrogenase Type I in Human Disease: a Novel Therapeutic Target," Minerva Endocrinologica, 30(1), Mar. 2005.

Office Action dated Mar. 19, 2012 in corresponding U.S. Appl. No. 12/170,104.

Office Action dated Mar. 19, 2012 in corresponding U.S. Appl. No. 12/170,116.

Office Action dated Mar. 19, 2012 in corresponding U.S. Appl. No. 12/170,132.

Office Action dated Mar. 19, 2012 in corresponding U.S. Appl. No. 12/170,148.

Office Action dated Mar. 19, 2012 in corresponding U.S. Appl. No. 12/170,157.

Bian et al., "High-Dose siRNAs Upregulate Mouse Eri-1 at both Transcription and Posttranscription Levels," PLoS One, 6(10), pp. 1-15, 2011.

Benitez-Del-Castillo et al., "Safety and Efficacy Clinical Trials for SYL1001, a Novel Short Interfering RNA for the Treatment of Dry Eye Disease," IOVS, 57(14), pp. 6447-6454, 2016.

Coelho et al., "Safety and Efficacy of RNAi Therapy for Transthyretin Amyloidosis," N. Engl. J. Med. 369(9), pp. 819-829, 2013.

Pecot et al., "RNA interference in the clinic: challenges and future directions," Nature Reviews, 11, pp. 59-67, 2011.

* cited by examiner

A

B

SEQUENCE LISTING

<160> NUMBER OF SEQ ID NOS: 28

<210> SEQ ID NO 1
<211> LENGTH: 19
<212> TYPE: DNA

<213> ORGANISM: Homo sapiens

<400> SEQUENCE: 1
aagcgcatct tctacttca                                                    19

<210> SEQ ID NO 2
<211> LENGTH: 19
<212> TYPE: RNA
<213> ORGANISM: Artificial
<220> FEATURE:
<223> OTHER INFORMATION: siRNA against TRPV1

<400> SEQUENCE: 2
aagcgcaucu ucuacuuca                                                    19

<210> SEQ ID NO 3
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (10)..(11)
<223> OTHER INFORMATION: uracil has a 2'-O methyl group
<220> FEATURE:
<221> NAME/KEY: misc_feature
<222> LOCATION: (16)..(17)
<223> OTHER INFORMATION: uracil has a 2'-O methyl group

<400> SEQUENCE: 3
aagcgcaucu ucuacuuca                                                    19

<210> SEQ ID NO 4
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (1)..(2)
<223> OTHER INFORMATION: adenine has a 2'-O methyl group
<220> FEATURE:
<221> NAME/KEY: misc_feature
<222> LOCATION: (7)..(7)
<223> OTHER INFORMATION: adenine has a 2'-O methyl group
<220> FEATURE:
<221> NAME/KEY: misc_feature
<222> LOCATION: (14)..(14)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 4
aagcgcaucu ucuacuuca                                                    19

<210> SEQ ID NO 5
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature

```
<222> LOCATION: (8)..(8)
<223> OTHER INFORMATION: n=deoxythymidine
<220> FEATURE:
<221> NAME/KEY: misc_feature
<222> LOCATION: (10)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (16)..(17)
<223> OTHER INFORMATION: n=deoxythymidine

<400> SEQUENCE: 5
aagcgcancn ncnacnnca                                          19

<210> SEQ ID NO 6
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (10)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (16)..(17)
<223> OTHER INFORMATION: n= deoxythymidine

<400> SEQUENCE: 6
aagcgcancn ncnacnnca                                          19

<210> SEQ ID NO 7
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 7
ucgccacgac augcucuugn n                                       21

<210> SEQ ID NO 8
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (13)..(13)
<223> OTHER INFORMATION: uracil has a 2'-O methyl group
<220> FEATURE:
```

```
<221> NAME/KEY: misc_feature
<222> LOCATION: (17)..(17)
<223> OTHER INFORMATION: uracil has a 2'-O methyl group

<400> SEQUENCE: 8
aagcgcaucu ucuacuuca                                                        19

<210> SEQ ID NO 9
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (17)..(17)
<223> OTHER INFORMATION: uracil has a 2'-O methyl group

<400> SEQUENCE: 9
aagcgcaucu ucuacuuca                                                        19

<210> SEQ ID NO 10
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (2)..(2)
<223> OTHER INFORMATION: adenine has a 2'-O methyl group
<220> FEATURE:
<221> NAME/KEY: misc_feature
<222> LOCATION: (7)..(7)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 10
aagcgcaucu ucuacuuca                                                        19

<210> SEQ ID NO 11
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (2)..(2)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 11
aagcgcaucu ucuacuuca                                                        19

<210> SEQ ID NO 12
<211> LENGTH: 19
<212> TYPE: RNA
<213> ORGANISM: Artificial
<220> FEATURE:
<223> OTHER INFORMATION: siRNA against TRPV1
```

```
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (11)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (16)..(17)
<223> OTHER INFORMATION: n=deoxythymidine

<400> SEQUENCE: 12
aagcgcancu ncnacnnca                                           19

<210> SEQ ID NO 13
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (11)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 13
aagcgcancu ncnacunca                                           19

<210> SEQ ID NO 14
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 14
aagcgcancu ucnacunca                                           19

<210> SEQ ID NO 15
<211> LENGTH: 19
<212> TYPE: RNA
<213> ORGANISM: Artificial
<220> FEATURE:
```

```
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 15
aagcgcancu ucuacunca                                          19

<210> SEQ ID NO 16
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 16
aagcgcancu ucuacunca                                          19

<210> SEQ ID NO 17
<211> LENGTH: 19
<212> TYPE: RNA
<213> ORGANISM: Artificial
<220> FEATURE:
<223> OTHER INFORMATION: siRNA against TRPV1

<400> SEQUENCE: 17
cgcaucuucu acuucaacu                                          19

<210> SEQ ID NO 18
<211> LENGTH: 19
<212> TYPE: RNA
<213> ORGANISM: Artificial
<220> FEATURE:
<223> OTHER INFORMATION: siRNA against TRPV1

<400> SEQUENCE: 18
gcgcaucuuc uacuucaac                                          19

<210> SEQ ID NO 19
<211> LENGTH: 19
<212> TYPE: RNA
<213> ORGANISM: Artificial
<220> FEATURE:
<223> OTHER INFORMATION: siRNA against TRPV1

<400> SEQUENCE: 19
aaagccaugc ucaaccugc                                          19

<210> SEQ ID NO 20
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
```

```
<222> LOCATION: (20)..(21)
<223> OTHER INFORMATION: n=deoxythymidine

<400> SEQUENCE: 20
ugaucgcagg aguaucuuun n                                              21

<210> SEQ ID NO 21
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 21
caagaucgca caggagagcn n                                              21

<210> SEQ ID NO 22
<211> LENGTH: 19
<212> TYPE: RNA
<213> ORGANISM: Artificial
<220> FEATURE:
<223> OTHER INFORMATION: siRNA against TRPV1; antisense to SEQ ID NOs
      2-5 and 8-15

<400> SEQUENCE: 22
ugaaguagaa gaugcgcuu                                                 19

<210> SEQ ID NO 23
<211> LENGTH: 19
<212> TYPE: RNA
<213> ORGANISM: Artificial
<220> FEATURE:
<223> OTHER INFORMATION: siRNA against TRPV1; antisense to SEQ ID No: 6
<220> FEATURE:
<221> NAME/KEY: misc_feature
<222> LOCATION: (1)..(1)
<223> OTHER INFORMATION: n=deoxythymidine
<220> FEATURE:
<221> NAME/KEY: misc_feature
<222> LOCATION: (6)..(6)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (18)..(19)
<223> OTHER INFORMATION: n=deoxythymidine

<400> SEQUENCE: 23
ngaagnagaa gangcgcnn                                                 19

<210> SEQ ID NO 24
<211> LENGTH: 19
<212> TYPE: RNA
<213> ORGANISM: Artificial
<220> FEATURE:
<223> OTHER INFORMATION: siRNA against TRPV1; antisense to SEQ ID NO: 16
<220> FEATURE:
<221> NAME/KEY: misc_feature
<222> LOCATION: (6)..(6)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
```

```
<400> SEQUENCE: 24
ugaagnagaa gangcgcuu                                              19

<210> SEQ ID NO 25
<211> LENGTH: 19
<212> TYPE: RNA
<213> ORGANISM: Artificial
<220> FEATURE:
<223> OTHER INFORMATION: siRNA against TRPV1: antisense to SEQ ID NO: 17

<400> SEQUENCE: 25
aguugaagua gaagaugcg                                              19

<210> SEQ ID NO 26
<211> LENGTH: 19
<212> TYPE: RNA
<213> ORGANISM: Artificial
<220> FEATURE:
<223> OTHER INFORMATION: siRNA against TRPV1: antisense to SEQ ID No: 18

<400> SEQUENCE: 26
guugaaguag aagaugcgc                                              19

<210> SEQ ID NO 27
<211> LENGTH: 19
<212> TYPE: RNA
<213> ORGANISM: Artificial
<220> FEATURE:
<223> OTHER INFORMATION: siRNA against TRPV1: antisense to SEQ ID NO: 19

<400> SEQUENCE: 27
gcagguugag cauggcuuu                                              19

<210> SEQ ID NO 28
<211> LENGTH: 21
<212> TYPE: RNA
<213> ORGANISM: Artificial
<220> FEATURE:
<223> OTHER INFORMATION: siRNA against TRPV1: antisense to SEQ ID NO: 20
<220> FEATURE:
<221> NAME/KEY: misc_feature
<222> LOCATION: (20)..(21)
<223> OTHER INFORMATION: n=deoxythymidine

<400> SEQUENCE: 28
aaagauacuc cugcgaucan n                                           21
```

SIRNA AND THEIR USE IN METHODS AND COMPOSITIONS FOR THE TREATMENT AND / OR PREVENTION OF EYE CONDITIONS

FIELD OF THE INVENTION

The present invention relates to the provision of siRNA products and their use in methods and compositions for the treatment and/or prevention of eye conditions related to high levels of expression and or activity of the transient receptor potential vanilloid (TRPV1) using RNA interference. Amongst others, eye conditions associated to ocular pain such as discomfort and altered sensitivity of the cornea following refractive surgery, use of contact lenses, dry eye syndrome, and Sjogren's syndrome, are to be mitigated.

BACKGROUND OF THE INVENTION

RNA interference (RNAi) is a naturally occurring regulatory mechanism of most eukaryotic cells that uses small double stranded RNA (dsRNA) molecules to direct homology-dependent gene silencing. Its discovery by Fire and Mello in the worm C. elegans {Fire, 1998} was awarded the Nobel prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defence mechanism used to prevent the expression of foreign genes and is commonly shared by diverse phyla and flora, where it is called post-transcriptional gene silencing. Since the discovery of RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Ma, 2005; Doench 2004; Lewis, 2003}. Once the mRNA has been cleaved, and due to the presence of unprotected RNA ends in the fragments, the mRNA is further cleaved and degraded by intracellular nucleases and will no longer be translated into proteins {Orban, 2005} while RISC will be recycled for subsequent rounds {Hutvagner, 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then. Also, considerable effort has been put into enhancing siRNA stability as this is perceived as one of the main obstacles for therapy based on siRNA, given the ubiquitous nature of RNAses in biological fluids. One of the main strategies followed for stability enhancement has been the use of modified nucleotides such as 2'-O-methyl nucleotides, 2'-amino nucleotides, nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability is often inversely proportional to efficacy (Parish, 2000), and only a certain number, positions and/or combinations of modified nucleotides may result in a stable silencing compound. As this is an important hurdle within siRNA-based treatments, different studies have been published which describe certain modification patterns showing good results, examples of such include EP1527176, WO2008/050329, WO2008/104978 or WO2009/044392, although many more may be found in the literature.

The Transient Receptor Potential Vanilloid-1 (TRPV1), also called Vanilloid Receptor 1 (VR-1), is a capsaicin-responsive ligand-gated cation channel, that was first discovered in 1997 (Caterina, 1997). TRPV1 is mainly expressed on sensory neurons and serves as a molecular detector for heat, capsaicin, protons, and endovanilloids (Caterina, 2001; Montell, 2002; Baumann, 2000). Although the inventors of the present application have also found TRPV1 expression in tissues from the lacrimal gland and ciliary body.

When TRPV1 is activated by agonists such as capsaicin and other factors such as heat, acidosis, lipoxygenase products or anandamide, calcium enters the cell and pain signals are initiated. Activation of the channel induces neuropeptide release from central and peripheral sensory nerve terminals, resulting in the sensation of pain, neurogenic inflammation, and sometimes, in smooth muscle contraction and cough. As a matter of fact, recent evidence suggests a role of TRPV1 in pain, cough, asthma and urinary incontinence (Jia, 2005). In fact, TRPV1 is a known target for treatments by analgesia in response to pain stimuli. Moreover, treatments designed to reduce expression levels of TRPV1 using different technologies have also been described in WO2004/042046, or (Schubert, 2005), with a focus on the treatment of pain.

Polymodal nociceptors are the most abundant nociceptor type found in the cornea. There exists pharmacological evidence that these receptor fibers express TRPV1 receptor because they respond to capsaicin, heat and acid. Moreover, high doses of capsaicin inactivate the response of corneal polymodal nociceptors to heat and acid whereas mechanical responsiveness remains unaffected. This suggests that TRPV1 receptors present in corneal polymodal nerve endings were selectively inactivated.

Therefore, it is likely that an important part of the acute nociceptive response to corneal injury and the sustained pain sensations that accompany inflammatory and irritative processes in this tissue are mediated by TRPV1 activation.

Furthermore, WO2007/045930 describes the use of TRPV1 specific siRNAs for treatment of ocular pathologies related to ocular pain and dry eye syndrome. However, the present invention provides improved products for reducing TRPV1 expression and consequent ocular discomfort. The advantage of treating these conditions with siRNA products vs traditional chemical inhibitors is that treatments based on siRNA will have a longer-lasting effect. This result is due to the fact that once the effector molecule is no longer present, the cell will have to synthesise new receptors from scratch; whereas traditional treatments would leave the levels of receptors on the cell membrane intact.

Due to current life-style, the number of people affected by ocular pathologies related to altered ocular sensitivity is quite high, and is expected to increase with aging of population. Refractive surgery and contact lens use often derive in altered corneal sensitivity and a sensation of dry eye by the patient. This is further aggravated by long working hours looking at computer screens and the use of air-conditioning systems which usually further dry the atmosphere. Also, the quantity and quality of tears decrease with age. Symptoms accompanying dry eye syndromes include itching, burning and irritation of the ocular tissues. A more severe form of dry eye occurs in patients with Sjogren's syndrome. The presence of one or different combinations of these sensations is termed ocular pain within the meaning of the present text. At present dry eye syndrome is estimated to affect over 10 million Americans.

DETAILED DESCRIPTION OF THE INVENTION

Figure 1:
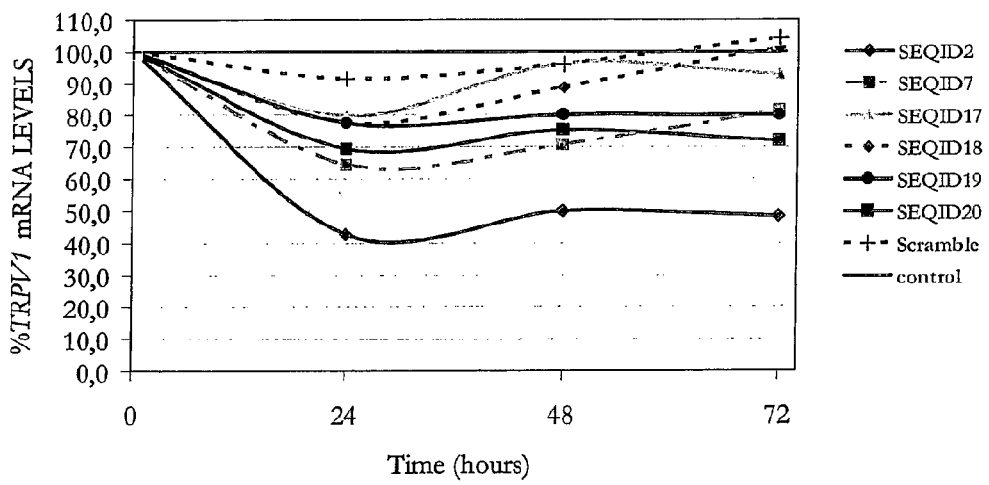
FIG. 1 is a diagram showing temporal expression profile of TRPV1, using Qrt-PCR, after transfection of HeLa cells with different siRNAs targeting TRPV1: a compound according to the present invention (SEQ ID NO: 2), a previously described compound targeting a different region (SEQ ID NO: 7), and another four siRNAs (SEQ ID NO: 17 to 20) designed to target TRPV1 and a scramble sequence used as a negative control. Two alternative representations of the same results are shown to ensure clarity, A and B.
Figure 1:
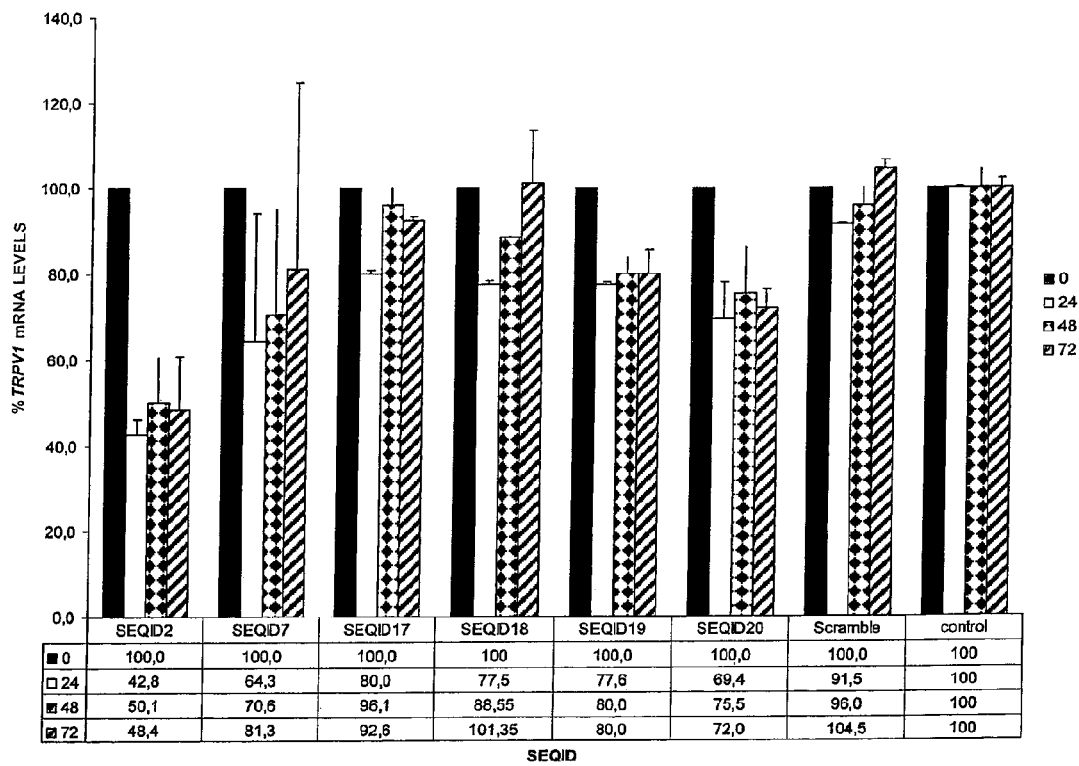

In a first aspect, the present invention relates to the provision of a dosage regimen for an siRNA molecule wherein said molecule specifically targets SEQ ID NO: 1 and reduces expression of the TRPV1 gene when introduced in a cell.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case TRPV1. Alternatively, a siRNA targets a gene when the siRNA hybridizes under stringent conditions to the gene transcript, i.e. its mRNA. Capable of hybridizing "under stringent conditions" means annealing to the target mRNA region, under standard conditions, e.g., high temperature and/or low salt content which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

Different transcript variants corresponding to TRPV1 have been identified. GenBank Accession Numbers corresponding to four TRPV1 transcripts produced by alternative splicing are: NM_080704 (NM_080704.3, GI:117306161), NM_018727 (NM_018727.5, GI:117306160), NM_080706 (NM_080706.3, GI:117306163) and NM_080705 (NM_080705.3, GI:117306162). Furthermore, ENSEMBL (MBL-EBI/Wellcome Trust Sanger Institute) has 5 further TRPV1 transcripts published: ENST00000174621, ENST00000310522, ENST00000344161, ENST00000399752, ENST00000399756, ENST00000399759, ENST00000425167.

The present invention provides dosage regimens for siRNAs which inhibit TRPV1 gene expression, these siRNAs being especially efficient compared to those already disclosed in the state of the art. Especially efficient meaning that they achieve higher degrees of inhibition and/or a more prolonged effect in time.

These siRNAs are designed against a target sequence common to all transcript variants of TRPV1 described in the preceding paragraph, and thus mediate RISC-mediated degradation of all possible mRNAs present in the cell encoding TRPV1 protein. Said preferred target region identified by the present invention is identified in SEQ ID NO: 1 (5'-AAGCGCATCTTCTACTTCA-3'). They are described in WO2011/148193.

Consequently, a siRNA according to the aspects of the present invention will preferably comprise a double stranded RNA molecule, whose antisense strand will comprise or consist of an RNA sequence substantially complementary to SEQ ID NO: 1, and its sense strand will comprise an RNA sequence complementary to the antisense strand, wherein both strands are hybridised by standard base pairing between nucleotides.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 80%, and between 80% up to 100% complementarity, for example, 85%, 86%, 87%, 88%, 89%, 90%, 91%, 92%, 93%, 94%, 95%, 96%, 97%, 98% or 99% complementarity, to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule.

As is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNases and imitate Dicer's natural substrate. Some authors recommend including overhangs on both 3' ends of the molecules, whereas others consider one overhang to be sufficient. Others have described the use of blunt-ended structures with specific modification patterns (EP 1527176, WO 2008/104978, and many others).

Overhangs may be comprised of between 1 and 5 nucleotides, typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO02/44321). These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the various aspects of the present invention refers to siRNA molecules targeting SEQ ID NO: 1 which comprise at least one overhang.

Another alternative embodiment of the various aspects of the present invention provides blunt-ended molecules.

Further, a preferred embodiment of the present invention relates to an siRNA comprising or consisting of a 19 nucleotide double-stranded structure targeting SEQ ID NO: 1. Surprisingly, said 19 nucleotide double-stranded RNAs have proven to be more resistant to degradation than previously described products with 21 nucleotides and 3' overhangs as may be seen in FIG. 5.

A particular embodiment of the present invention relates to a 19 nucleotide double-stranded blunt-ended siRNA targeted against SEQ ID NO: 1. In a further particular embodiment this compound is identified as SEQ ID NO: 2 (5'-AAGCGCAUCUUCUACUUCA-3'). In a further preferred embodiment, the antisense strand of this siRNA is at least 80%, preferably at least 90%, complementary to SEQ ID NO: 1.

Furthermore, as described in the section termed background of the art, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production. The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNases are also able to reduce induction of immune recognition of subsequent response. However, insertion of chemically modified nucleotides in a siRNA may also result in decreased silencing efficacy as described in the previous section, and hence must be approached with caution.

Consequently, in a preferred embodiment of the various aspects of the present invention, the siRNA further comprises at least one nucleotide with a chemical modification.

Preferred chemical modifications which enhance stability and reduce immunogenic effects include 2'-O-methyl nucleotides, 2'-fluoro nucleotides 2'-amino nucleotides, 2'-deoxy nucleotides, nucleotides containing 2'-O or 4'-C methylene bridges. Also, the modification of the ribonucleotide backbone connecting adjacent nucleotides by the introduction of phosphorothioate modified nucleotides. A further preferred chemical modification within the meaning of the present invention relates to the substitution of uracyl ribonucleotides with deoxythymidine (deoxyribonucleotides). In another preferred embodiment of the present invention, the at least one chemically modified nucleotide is on the sense strand, on the antisense strand or on both strands of the siRNA.

Accordingly, in one embodiment, the siRNA is selected from SEQ ID. NO. 3, 4, 5, 6, 8, 9, 10, 11, 12, 13, 14, 15 or 16.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the various aspects of the invention can be expressed within cells from eukaryotic promoters. Recombinant vectors capable of expressing the siRNA molecules can be delivered and persist in target cells. Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides. Delivery of siRNA molecule expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of siRNA targeting SEQ ID NO. 1 in the preparation of a medicament for use in a method of treatment of an eye condition characterised by increased expression and/or activity of TRPV1 wherein the siRNA is administered according to the dosage regimen disclosed herein. The method comprises inhibiting expression of TRPV1 in a patient. The term inhibition is used to indicate a decrease or downregulation of expression or activity. Preferably, the eye condition is ocular pain. In one embodiment, the eye condition is selected from the group comprising ocular discomfort and altered sensitivity of the cornea following refractive surgery, use of contact lenses, dry eye syndrome, Sjogren's syndrome, and other eye pathologies.

Therapeutic treatment with siRNAs directed against TRPV1 mRNA is expected to be beneficial over small molecule topical ocular drops by increasing the length of time that effect is observed, thereby allowing less frequent dosing and greater patient compliance. This is especially important in cases such as dry eye syndrome and altered corneal sensitivity as they are often chronic conditions.

Bearing in mind the preparation of such a medicament, the siRNA of the various aspects of the present invention may be formulated. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eyedrops, a gel, lotion, cream or ocular inserts. Other administration forms to the eye may include injection into the eye.

A further preferred embodiment of the various aspects of the present invention relates to an siRNA specifically targeting SEQ ID NO: 1 as described in the preceding paragraphs, for use as a medicament for the treatment of an eye condition characterised by increased expression and/or activity of TRPV1 wherein the siRNA is administered according to the dosage regimen disclosed herein. As described above, it may be an siRNA comprising or consisting of a 19 nucleotide double-stranded structure targeting SEQ ID NO: 1. This siRNA may be blunt-ended. Preferably, the siRNA is SEQ ID NO: 2. Other siRNA for use according to the invention may be selected from SEQ ID. NO. 3, 4, 5, 6, 8, 9, 10, 11, 12, 13, 14, 15 or 16.

Within the context of the present invention, to "specifically target" a sequence the siRNA of the invention preferably comprises at least the same seed sequence. Thus, any sequence according to the invention that specifically targets SEQ ID No. 1 is preferably identical in positions 2-8 of the antisense strand.

Notwithstanding the above, the siRNAs of the various aspects of the present invention may be used to silence TRPV1 expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly(lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. The preferred compositions of the invention are aqueous solutions, specifically saline solutions such as phosphate-buffered saline (PBS) with a pH range of about 7.0 to about 7.4, preferably with a pH of 7.2±0.5.

A siRNA molecule of the invention may be complexed with membrane disruptive agents and/or a cationic lipid or helper lipid molecule.

Delivery systems which may be used with the invention include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose generally depends on the type of disease, the composition used, the route of administration, the type of mammal being treated, the physical characteristics of the specific mammal under consideration, concurrent medication, and other factors that those skilled in the medical arts will recognize.

In particular, it is known that in addition to dosage, the administration schedule is an important determinant of effective downregulation by siRNA molecules.

The inventors have developed an effective dosage schedule for administration of a siRNA for the treatment of an eye condition characterised by increased expression and/or activity of TRPV1, in particular dry eye and or ocular pain, which avoids side effects and can be safely administered. Thus, administration of an siRNA molecule wherein said molecule specifically targets SEQ ID NO: 1 and reduces expression of TRPV1 gene when introduced in a cell according to the dosage regimens described herein leads to clinical improvement.

As used herein an "effective dosage schedule" refers to the amount of siRNA of the invention sufficient to treat or manage an eye disorder associated to overexpression of TRPV1. For treatment of dry eye and/or ocular pain in humans, it is preferred to reduce levels of ocular disease as measured by different parameters known to those skilled in the art, for example using OSDI (ocular surface index) questionnaire (for dry eye) and/or VAS (visual analogical scale) for ocular pain. Any reduction in these levels as compared to pretreatment levels is advantageous, whether the compounds of the invention are delivered alone, or in combination with another suitable therapeutic. (e.g., the invention contemplates a decrease in OSDI and/or VAS greater than about 5%, about 10%, about 25%, about 30%, about 35%, about 40%, about 50%, or about 60% of pretreatment IOP).

A therapeutically effective amount may also refer to the amount of an siNA sufficient to delay or minimize the onset of an eye disorder associated with dry eye and/or ocular pain. A therapeutically effective amount may also refer to the amount of the therapeutic agent that provides a therapeutic benefit in the treatment or management of an eye disorder associated with dry eye and/or ocular pain. Further, a therapeutically effective amount with respect to an siNA of the invention means that amount of therapeutic agent alone, or in combination with other therapies, that provides a therapeutic benefit in the treatment or management of an eye disorder associated with dry eye and/or ocular pain. Used in connection with an amount of an siNA of the invention, the term can encompass an amount that improves overall therapy, reduces or avoids unwanted effects, or enhances the therapeutic efficacy of or synergizes with another therapeutic agent.

A therapeutic benefit in the treatment or management of an eye disorder such as dry eye and/or ocular pain is the sustained decrease in pain and/or undesirable sensations. Given that siRNA will decrease the levels of TRPV1 receptors within the cell, once the treatment stops the cell must re-synthesise new receptors before pain sensations will be perceived. As such therapies based on siRNA treatments will have a more sustained effect. This is considered a significant enhancement of the therapeutic efficacy.

An additional benefit of using siRNA is the minimum probability of side effects or acute toxicity issues derived from its presence in systemic circulation, often associated with different eyedrop-based treatments. This is due to the fact that when the compound enters the bloodstream, it will be rapidly degraded by RNAses present in the blood.

On the other hand, the fact that the formulation described herein can be offered in single dose vials, means incorporation antimicrobial preservatives, present in the majority of formulations on the market today, and which produce a certain intolerance in some patients, making it necessary to stop the treatment. Both issues are especially important when bearing in mind that conditions like dry eye and or ocular pain are often chronic and therefore so is the treatment.

One of the preferred administration routes is topical, by instillation directly to the eye, preferably using eye drops. As described above, therapeutic treatment with siRNAs directed against TRPV1 mRNA is expected to be beneficial over small molecule topical ocular drops by increasing the length of time that effect is observed, thereby allowing less frequent dosing and greater patient compliance. When the siRNA is administered directly to the eye, generally an amount of about 0.01 mg to about 100 mg per day and per eye can be administered. In one embodiment, the amount administered per day and per eye is about 0.1 mg to about 10 mg. In another embodiment, about 0.04 mg to 80 mg, about 0.04 mg to about 20 mg, about 0.08 mg to about 10 mg, about 0.08 mg to about 1.2 mg, about 0.3 to about 0.9 mg, or about 0.08 mg to about 0.9 mg, per eye per day of siNA is administered.

In one embodiment, the dosage is about 0.5 mg to about 1.5 mg. In one embodiment, the dosage is about 0.3 to 0.9 mg, preferably about 0.6 mg to about 0.9 mg. Alternatively a preferred dosage is about 0.6 mg or about 0.9 mg per eye per day.

One of the preferred administration routes as mentioned above is via the use of eyedrops. In one embodiment these eyedrops have a volume of between 25 and 50 microliters containing the given dose of compound, preferably between 26 and 40 microliters. Preferably, commercial eyedroppers may be used in the final presentation of the medicine, and the resulting volume would be between about 30 and about 33 microliters per drop. In an additionally preferred embodiment the eyedrops are delivered in a volume of about 40 µl. In an additional embodiment the composition of the invention comprises an siRNA such as that of SEQ ID NO: 2 in an acceptable solution such as phosphate-buffered saline at a concentration of from about 7.5 to about 22.5 mg/ml, or alternatively from about 15 mg/ml to about 22.5 mg/ml. The compositions of the invention can comprise the above concentrations of siRNA in PBS and optionally pharmaceutically acceptable excipients such as for example benzalkonium chloride.

Treatment at the dosages above may be administered for 1, 2, 3, 4, 5, 6, 7, 8, 9, 10, 11, 12, 13, 14, 15, 16, 17, 18, 19, 20 or more days. Preferably, administration is for 10-15 days, most preferably for 10 days. Administration may be followed by a rest period, for example a rest period of 7 days before continuation of the treatment. Alternatively, given that dry eye and/or ocular pain are often chronic conditions, the dosages may be administered on a daily basis during a long period resulting in a chronic administration. Accordingly, administration may be continued for more than 4 weeks on a daily basis, or alternatively, administration may be continued for more than 4 weeks but not on a daily basis. The precise schedule can be determined in accordance with the severity of the chronic condition.

However, as explained above, administration routes other than directly to the eye can also be used. The precise dosage and administration schedule to be employed in the formulation will also depend on the route of administration, but the dosages above can be employed and generally an amount of about 0.01 mg to about 100 mg per day and per eye can be administered. A skilled person would understand that the precise dosage and administration schedule to be employed also depends on the seriousness of the disorder, and should be decided according to the judgment of the practitioner and each patient's circumstances. It is also understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agents. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In preferred embodiments, the compositions of the invention are formulated in a solution, preferably a buffered saline solution such as PBS, or a gel for topical administration to the eye, such as, for example, in the form of eyedrops. In such embodiments, the formulations may be cationic emulsions and/or contain biopolymers including, but not limited to, poly(lactide-co-glycolide), carbopol, hialuronic acid and polyacrylic acid.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention relates to a pharmaceutical composition wherein said composition comprises at least an siRNA targeting SEQ ID NO: 1 at a specific dosage schedule, as has been described in the preceding paragraphs.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

The siNA compounds of the invention can also be provided in kits that comprise a dispenser with an orifice for dispensing specific dosages of the siNA compound in a droplet of predetermined volume. In a preferred embodiment the siNA compounds of the invention are siRNAs targeted against SEQ ID NO: 1. In a further embodiment the dispensers within the kit of the invention provide a composition comprising or consisting of SEQ ID NO: 2. In another embodiment the kit can comprise a collection of single use dispenser, for example for use during one month, in this specific case, the case would contain 30 single use dispensers. The droplet can range from about 50 µl to about 100 µl in volume. The dispenser can be a single use dispenser and comprise between about 1 mg and about 2 mg of the siNA compounds of the invention, and optionally also comprise one or more pharmaceutically acceptable diluents, and optionally one or more excipients. The composition contained in the dispenser can comprise a concentration of between about 7.5 mg/ml to about 22.5 mg/ml of the siNA compound of the invention. Alternatively, the dispenser can be designed to be used for one month or more and the volumes contained will increase accordingly to provide the equivalent number of doses. The kits of the invention can also comprise instructions specifying that a dosage of the siRNA compound of between about 0.3 mg and about 0.9 mg in 1 droplet is to be applied to each eye. The instructions can further specify that the droplets are applied to each eye once a day, twice a day, three times a day, or four times a day, and that the application to each eye is to take place daily, every other day, once a week, twice a week, three times a week, every other week, or once a month.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

The invention is further described in the following non-limiting examples.

EXAMPLES

In Vitro Analysis

In order to find a particularly effective target sequence for siRNAs to silence TRPV1 (which obtain important inhibition of gene expression), six different siRNAs were tested. These siRNAs are described as SEQ ID NO: 2, SEQ ID NO: 7 and SEQ ID NO: 17 to 20.

SEQ ID NO: 2 is an siRNA targeting SEQ ID NO: 1 according to the present invention having the following sequence:

```
Sense:       5'-AAGCGCAUCUUCUACUUCA-3'
Antisense:   5'-UGAAGUAGAAGAUGCGCUU-3'
```

SEQ ID NO: 7 (5'-UCGCCACGACAUGCUC-UUGdTdT-3') corresponds to a classical siRNA molecule (21 nucleotides in length containing 3' overhangs made of deoxythymidine) previously described in WO 2007/045930 to effectively target TRPV1 and reduce ocular response to capsaicin stimuli. SEQ ID NO: 17 to 19 correspond to siRNAs designed against TRPV1 according to different algorithms available in the art such as those described by Reynolds et al. 2004 or Ui-Tei et al 2004, and others. SEQ ID NO: 20 is a commercially available siRNA supplied by Ambion and designed against TRPV1.

```
                                SEQ ID NO: 17
Sense:       5'-CGCAUCUUCUACUUCAACU-3'
Antisense:   5'-AGUUGAAGUAGAAGAUGCG-3'

SEQ ID NO: 18
Sense:       5'-GCGCAUCUUCUACUUCAAC-3'
Antisense:   5'-GUUGAAGUAGAAGAUGCGC-3'

SEQ ID NO: 19
Sense:       5'-AAAGCCAUGCUCAACCUGC-3'
Antisense:   5'-GCAGGUUGAGCAUGGCUUU-3'

SEQ ID NO: 20
Sense:       5'-UGAUCGCAGGAGUAUCUUUdTdT-3'
Antisense:   5'-AAAGAUACUCCUGCGAUCAdTdT-3'
```

As a model to test effectiveness of the above described siRNA, HeLa (human cervix adenocarcinoma) cell cultures were used. HeLa cells were transfected with 100 nM of different compounds and Lipofectamine 2000 as a transfectant agent. All transfections were done following standard manufacturer's conditions. In the same transfection a different scramble siRNA was used as control. Cell pellets were collected at 24, 48, and 72 hours to evaluate possible variations in protein levels and processed by real-time PCR. In order to quantify the results obtained by real-time Qrt-PCR, we used the Comparative Threshold Method.

As results show (FIG. 1), an siRNA directed against target sequence SEQ ID NO: 1, is much more efficient in terms of TRPV1 gene silencing than previously described siRNA products directed against a different region of the same gene. Moreover this effect is sustained in time, as at 72 hours post-transfection there is still significant downregulation of mRNA levels. This duration of the effect is unpredictable and is sequence specific.

With the objective of providing further improved products, different chemical modifications were introduced on the above product, according to the description below:

```
                      SEQ ID NO: 3
Sense:     5'-AAGCGCAUCUUCUACUUCA-3'
Antisense: 5'-UGAAGUAGAAGAUGCGCUU-3', SEQ ID NO: 4
Sense:     5'-AAGCGCAUCUUCUACUUCA-3'
Antisense: 5'-UGAAGUAGAAGAUGCGCUU-3', SEQ ID NO: 8
Sense:     5'-AAGCGCAUCUUCUACUUCA-3'
Antisense: 5'-UGAAGUAGAAGAUGCGCUU-3', SEQ ID NO: 9
Sense:     5'-AAGCGCAUCUUCUACUUCA-3'
Antisense: 5'-UGAAGUAGAAGAUGCGCUU-3', SEQ ID NO: 10
Sense:     5'-AAGCGCAUCUUCUACUUCA-3'
Antisense: 5'-UGAAGUAGAAGAUGCGCUU-3', SEQ ID NO: 11
Sense:     5'-AAGCGCAUCUUCUACUUCA-3'
Antisense: 5'-UGAAGUAGAAGAUGCGCUU-3',
```

Wherein the underline represents bases comprising a 2'-Omethyl group.

```
                      SEQ ID NO: 5
Sense:     5'-AAGCGCAdTCdTdTCdTACdTdTCA-3'
Antisense: 5'-UGAAGUAGAAGAUGCGCUU-3', SEQ ID NO: 6
Sense:     5'-AAGCGCAdTCdTdTCdTACdTdTCA-3'
Antisense: 5'-dTGAAGdTAGAAGAdTGCGCdTdT-3', SEQ ID NO: 12
Sense:     5'-AAGCGCAdTCUdTCdTACdTdTCA-3'
Antisense: 5'-UGAAGUAGAAGAUGCGCUU-3', SEQ ID NO: 13
Sense:     5'-AAGCGCAdTCUdTCdTACUdTCA-3'
Antisense: 5'-UGAAGUAGAAGAUGCGCUU-3', SEQ ID NO: 14
Sense:     5'-AAGCGCAdTCUUCdTACUdTCA-3'
Antisense: 5'-UGAAGUAGAAGAUGCGCUU-3', SEQ ID NO: 15
Sense:     5'-AAGCGCAdTCUUCUACUdTCA-3'
Antisense: 5'-UGAAGUAGAAGAUGCGCUU-3', SEQ ID NO: 16
Sense:     5'-AAGCGCAdTCUUCUACUdTCA-3'
Antisense: 5'-UGAAGdTAGAAGAdTGCGCUU-3',
```

Wherein some or all uracyl nucleotides have been substituted for deoxythymidine nucleotides.

These compounds were tested in immunogenicity assays along with SEQ ID NO: 2 (the same compound without any modified nucleotides). Results showed that all these compounds significantly reduced induction of an immune response in peripheral blood mononuclear cells. Moreover, most compounds induced a response which was at its highest levels, as low as that produced by siRNAs which have advanced through human clinical trials (bevasiranib and Sirna-027) which were included in the assays as a control.

As varying degrees of modification can alter gene silencing ability of siRNAs, these compounds were further tested for their RNA interfering capacity by transfection into HeLa cells, and resulting TRPV1 mRNA levels were measured according to the method described in preceding paragraphs.

Figure 2:
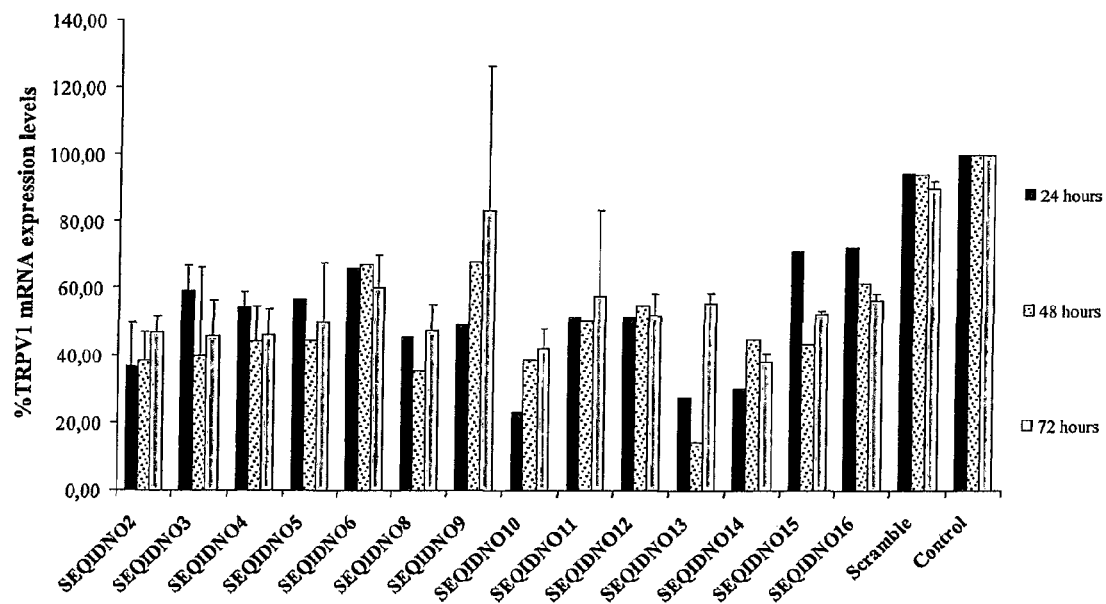
FIG. 2 is a diagram showing temporal expression profile of TRPV1, using Qrt-PCR, after transfection of HeLa cells with different siRNAs of the present invention: SEQ ID NO: 2 to SEQ ID NO: 6, and SEQ ID NO: 8 to SEQ ID NO: 16, and a scramble sequence used as a negative control.

As may be seen in FIG. 2, all compounds retain the ability to efficiently decrease TRPV1 mRNA levels in varying degrees.

Figure 5:
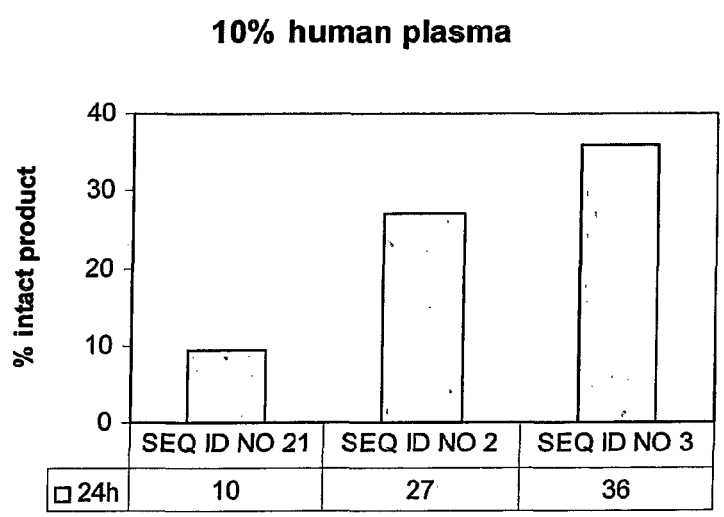
FIG. 5 is a graph showing the amount of intact product (%) remaining after being exposed to 10% plasma for 24 hours.

A further unexpected beneficial effect derived from the above described compounds is their enhanced resistance to degradation by RNases as may be seen in FIG. 5.

For these experiments, compounds were suspended in 10% human plasma in PBS at a final concentration of 2 µM and incubated for 24 hours at 37° C. Samples were then analysed using HPLC-UV and the amount of remaining intact product is determined. As may be observed in FIG. 5, the 19 nucleotide double-stranded compound of SEQ ID NO: 2 (without any chemical modification) is almost 3 times more resistant to degradation than previously described SEQ ID NO: 21: 5'-CAAGAUCGCACAGGAGAGCdTdT-3' (also described in WO 2007045930) which comprises 3' overhangs. This effect is further enhanced for compound of SEQ ID NO: 3, which includes some chemically modified nucleotides as described in preceding paragraphs.

In Vivo Analysis

Animal models of dry eye and ocular pain often make use of rabbits, in this case New Zealand White rabbits. To this end, a further advantage of the siRNAs of the present invention is that the target sequence, SEQ ID NO: 1, is a highly conserved region of the TRPV1 gene, throughout different animal sequences. In fact, this sequence is identical between human and rabbit, making this animal model especially suitable for the study of said diseases.

The experiment described below was performed using a standard model of ocular pain known to an expert in the field (Gonzalez et al. 1993). Briefly, pain was induced using instillation of 30 µl of a solution of 1% capsaicin (a known agonist of TRPV1) to the eye using an appropriate micropipette. Due to ethical considerations, animals to be treated with capsaicin had previously received a dose of capsazepine 5 mM, a known capsaicin antagonist, or 40 µl of a solution containing the compound to be tested. Therefore analgesic effect is measured in comparison to capsazepine as a reference treatment.

Test and reference items were instilled once a day from Day 1 to Day 3 and twice a day on Day 4 (pace out of 60 min) in the right eyes. At Day 4, 15 minutes following the last instillation, corneal pain was induced in the right eye of the animals by a single instillation of capsaicin 1%. The contralateral eye was instilled with PBS throughout the study and served as control.

To measure response to pain, palpebral opening was measured. It is considered that the eye is closed in response to pain, and as pain sensations subside the palpebral opening will increase back to normal levels. The palpebral opening was measured before treatment (baseline), just before pain induction and then 1, 5, 10, 15, 20, 25, 30, minutes after pain induction.

Figure 3:
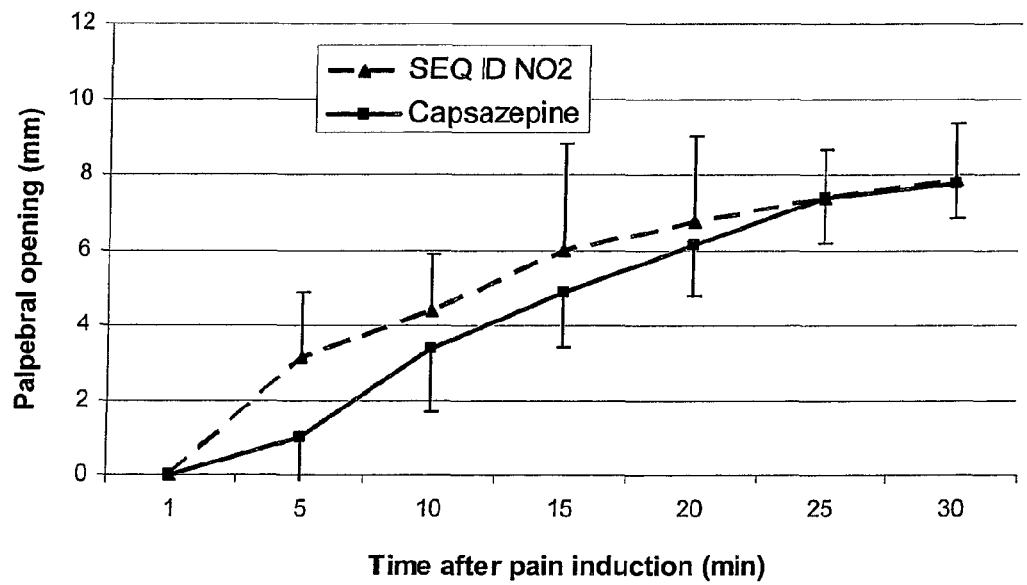
FIG. 3 shows a timeline with the palpebral opening measured in mm of the eyes from rabbits treated with a compound of the present invention (SEQ ID NO: 2) in comparison to capsazepine, an accepted specific analgesic for TRPV1 dependent pain, after stimulation with capsaicin.
Figure 4:
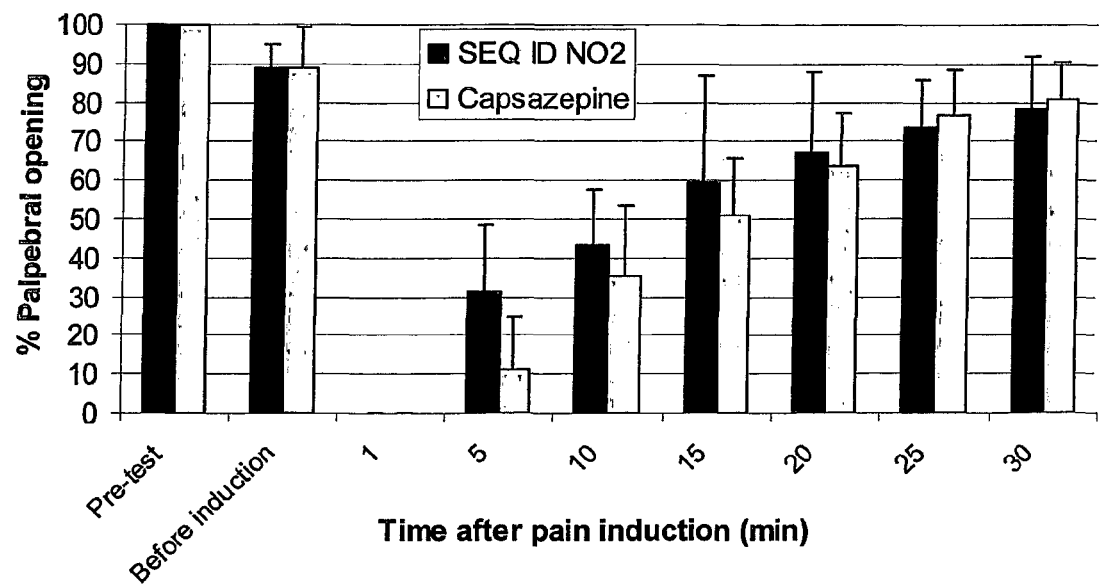
FIG. 4 is a graph showing the ratio (%) with respect to pre-test values, of the palpebral opening after pain induction with capsaicin, resulting from treatment with a compound of the present invention (SEQ ID NO: 2) and capsazepine.

As may be seen from FIGS. 3 and 4, a compound according to the present invention was tested, specifically the compound of SEQ ID NO: 2, and was observed to induce a higher analgesic effect than capsazepine (eye recovery as measured by degree of palpebral opening). Therefore this compound has proven to be an effective therapeutic treatment for ocular discomfort.

Furthermore, another in vivo experiment was performed in which the compounds of the present invention (SEQ ID NO: 2, SEQ ID NO: 4 and SEQ ID NO: 5) were administered to rabbits eyes, along with SEQ ID NO: 21, previously described in WO 2007045930. In this case, rabbits (6 animals per treatment group) received a daily administration of the compound during 3 consecutive days. On the third day, two hours after the last instillation, animals were sacrificed. Ocular tissues from these rabbits were recovered and presence of TRPV1 specific mRNA was analysed using RT-PCR. The following table (Table 1) shows the levels of TRPV1 gene silencing achieved in a given tissue expressed as a ratio of the % of inhibition achieved with reference compound SEQ ID NO: 21.

TABLE 1

|  | SEQ ID NO: 2 | SEQ ID NO: 4 | SEQ ID NO: 5 |
|---|---|---|---|
| Lacrimal gland | 3.06 | 3.15 | 1.92 |
| Ciliary body | 6.54 | 2.48 | 3.57 |

As is clear from these results, the compounds of the present invention are much more effective when silencing TRPV1 gene expression in ocular tissues than previously described compounds.

The higher efficacy together with the longer lasting effect of the compounds of the invention, should provide advantageous dose regimes, as allowing more time between doses would significantly improve patients' quality of life.

Another experiment was performed to evaluate the tissue distribution and plasma exposure in New Zealand White rabbits following ocular administration of SEQ ID NO: 2 in PBS. Materials and methods employed are specified in the following table (Table 2).

TABLE 2

Materials and methods to evaluate the tissue distribution and plasma exposure in New Zealand White rabbits following ocular administration of SEQ ID NO: 2 in PBS

| Test animals | Species: New Zealand White Rabbit<br>No. of animals/sex/administration route: 6 animals/3 male/3 female/ocular eye drop |
|---|---|
| Test substance | Drug: SEQ ID NO: 2 |
| Treatment | Dose: 0.9 mg/eye/adm<br>Administration: ocular (eye drop)<br>Frequency: once<br>Duration: 30 minutes |
| Formulation | Description: SEQ ID NO: 2 is formulated in sterile Phosphate Buffered Saline (PBS) at a concentration of 22.5 mg/mL |
| Sampling | Time point: 5 and 30 min post dose (tissue and plasma collection).<br>Storage conditions: −80° C. |
| Bioanalytical Assay | Method: Anion-Exchange High Performance Liquid Chromatography (AEX-HPLC) with fluorescence detection developed for SEQ ID NO: 2<br>Limit of Detection: 0.25 ng/g in tissue and 0.15 ng/mL in plasma |

All calculations were done using the molecular weight of the sodium salt of SEQ ID NO: 2. The calculation of the SEQ ID NO: 2 concentrations were done in three different ways:
1. Based on the peak area of intact non-metabolized antisense strand of SEQ ID NO: 2 (parent compound). This value is a marker for the amount of the parent compound that is unchanged in the tissue.
2. Based on the peak area of intact 5'-phosphorylated antisense strand of SEQ ID NO: 2. This value is a marker for the amount of the parent compound that is present in the cytoplasmic compartment and is activated by 5'-phosporylation.
3. Based on the total peak area. This value summarizes all intact and metabolized SEQ ID NO: 2 which are present in the sample.

Samples of liver, kidney cortex and medulla, lung, ciliary body, retina, iris, lacrimal gland, cornea, aqueous and vitreal humour, ganglion, plasma and urine were collected 5 and 30 minutes post dose. After one ocular administration of SEQ ID NO: 2 to rabbits (n=6) the results indicated:

Systemic exposure of SEQ ID NO: 2 was detected in plasma and systemic tissue samples at 5 and 30 minutes post dosing to the eye at concentrations below 1 ng/g (see Table 3).

TABLE 3

Mean concentrations for SEQ ID NO: 2 parent compound after ocular administration to rabbits.

|  | Time Point [min] | N | Liver [ng/g] | Kidney Medulla [ng/g] | Kidney Cortex [ng/g] | Lung [ng/g] | Plasma [ng/mL] |
|---|---|---|---|---|---|---|---|
| Mean Concentration | 5 | 6 | 0.42 | 0.16 | 0.34 | 0.04 | 0.34 |
| Standard Deviation |  |  | 0.48 | 0.25 | 0.56 | 0.13 | 0.32 |
| Mean Concentration | 30 | 6 | 0.60 | 0.77 | 0.00 | 0.40 | 0.09 |
| Standard Deviation |  |  | 0.63 | 1.96 | 0.00 | 0.13 | 0.05 |

SEQ ID NO: 2 could be detected in all eye tissues and fluids 5 minutes post dosing and at strongly decreased concentrations 30 minutes post dose (see Table 4).

TABLE 4

Mean concentrations for SEQ ID NO: 2 parent compound after ocular administration to rabbits.

|  | Time Point [min] | N | Ciliary Body [ng/g] | Retina [ng/g] | Iris [ng/g] | Lacrimal Gland [ng/g] | Cornea [ng/g] |
|---|---|---|---|---|---|---|---|
| Mean Concentration | 5 | 6 | 431.6 | 840.8 | 317.0 | 1473.8 | 3684.2 |
| Standard Deviation |  |  | 318.3 | 667.0 | 193.2 | 2178.8 | 984.8 |
| Mean Concentration | 30 | 6 | 4.3 | 3.7 | 2.1 | 132.4 | 59.3 |
| Standard Deviation |  |  | 4.8 | 3.7 | 2.3 | 394.6 | 71.0 |

Figure 6:
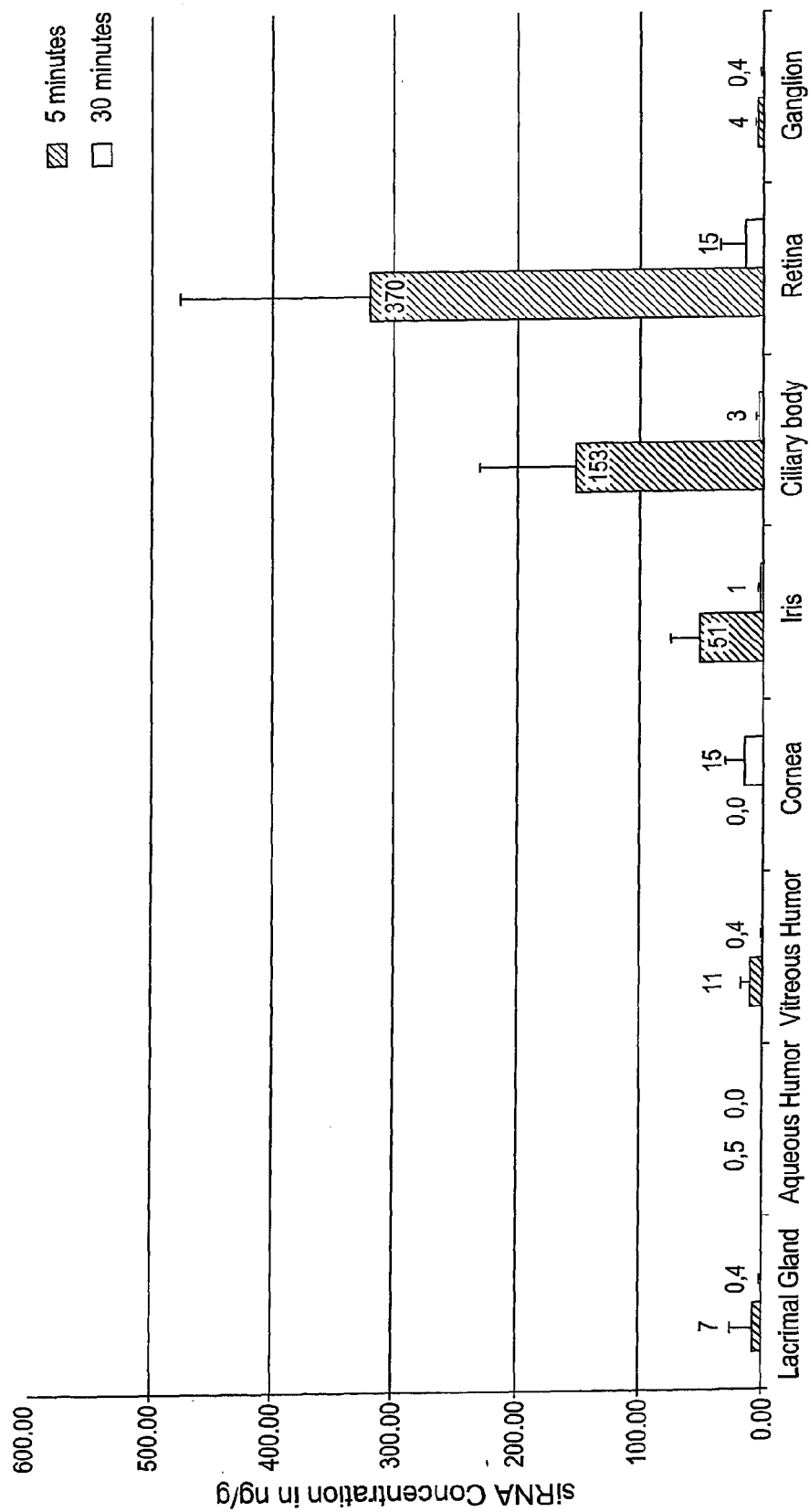
FIG. 6 is a graph showing the concentration of SEQ ID NO: 2 in eye tissues based on 5-phosphorylated intact antisense strand, which means the amount of the intact non-metabolized antisense strand of SEQ ID NO: 2 (parent compound) that is present in the cytoplasmic compartment and is activated by 5'-phosporylation. Left bar: 5 min; right bar: 30 min.

In retina, iris, ciliary body and lacrimal gland the 5'-phosphorylated antisense-(as) strand was detected at 5 and 30 minutes post dose indicating cytoplasmic delivery of the siRNA in these tissues (activated siRNA in target cell compartment) (see FIG. 6).

These data reflects that following ocular administration of SEQ ID NO: 2, animals present activated SEQ ID NO: 2 distributed in all eye tissues which can be detected 5 minutes post dosing.

Analysis in Humans

Initially the ocular tolerance of the compound according to SEQ ID NO: 2 was assessed in 30 healthy human adults.

The study was organised into two periods. During the first period an initial safety evaluation was made using a single dose of the investigational product, followed by a second period with a multi-dose administration.

Period 1, single dose: controlled with no intervention, and randomisation of the eye receiving the administration. Each volunteer was his/her own control, given the fact that the test item was administered to just one eye whilst the other eye received no intervention, however the safety evaluation tests were conducted. The ophthalmologist making the safety evaluation was blind to the drug administration. Product absorption into the bloodstream was determined.

Period 2, multi-dose: Open, parallel and controlled. The treated eye was randomised. The evaluator was blind as to the investigational product administration site. The eye before drug administration and the other eye were both considered as controls. During this stage the local and systemic safety were evaluated, in addition to absorption and, where appropriate, the pharmacokinetics of the investigational product.

The second stage commenced once the safety and pharmacokinetics of the first stage had been evaluated. The results for the first stage established the need to continue with the pharmacokinetic evaluation during the second stage.

30 adults were distributed in different treatment groups and received either a single 26.6 μl eyedrop containing a 600 μg dose of compound in one eye (period 1), or a daily dose during one week of 600 or 900 μg of compound per eye (period 2), administered in a volume of 26.6 μl or 40 μl, respectively. Period 1 had 6 volunteers and period 2 had 24 volunteers, divided into two cohorts with a different dose level applied to each half of the group. Period 1 comprises a single dose and period 2 comprises 7 doses in total (one administration per day).

Local tolerance assessment was based on the frequency of alterations (local adverse effects) detected on the eye surface during explorations performed 24 hours after last dose administration in Period 2 and 72 hours after the single dose instillation in period 1. Good tolerance was defined as the absence of grade 3 toxicity or higher, on the CTCAEv3 scale (Common Terminology Criteria for Adverse Events).

A Chi Square test was used to determine the relationship between the local adverse effects and the medication, considering whether or not symptoms or local signs had appeared in each eye (regardless of the number of symptoms), in relation to the treatment. The analysis considered the presence of an adverse effect in each eye, if at least one had occurred (see Table 5).

TABLE 5

Analysis of the local adverse effects on the eyes, in relation to the administration of the medication.

| | | | Adverse effect | | |
|---|---|---|---|---|---|
| | | | no | Yes | Total |
| Treated | no | Count | 26 | 4 | 30 |
| | | Expected frequency | 24.5 | 5.5 | 30.0 |
| | | % of adverse effect | 53.1% | 36.4% | 50.0% |
| | | Residual | 1.5 | −1.5 | |
| | Yes | Count | 23 | 7 | 30 |
| | | Expected frequency | 24.5 | 5.5 | 30.0 |
| | | % of adverse effect | 46.9% | 63.6% | 50.0% |
| | | Residual | −1.5 | 1.5 | |
| Total | | Count | 49 | 11 | 60 |
| | | Expected frequency | 49.0 | 11.0 | 60.0 |
| | | % of adverse effect | 100.0% | 100.0% | 100.0% |

With regard to the development of local alterations (local adverse effects), no differences were observed between the treated eye and the untreated eye, obtaining a Pearson's Chi Square of 1.002 (p=0.317).

No drug-related ocular surface alterations were observed in any period of the trial; therefore local tolerance was excellent when administered as single or multiple doses for up to seven days as eyedrops.

A further object of this trial was to assess systemic tolerance to the compound, by monitoring repercussions on the analytical parameters, on the physical examination, vital signs and the electrocardiogram following treatment.

Blood and urine analyses were performed during the selection process, before administration of the medication, and at the final examination, in the days following the final administration of SEQ ID NO: 2. A study was made of the variation in the analytical parameters between the selection period and the final examination, using Student's t test for related data. The following table shows the mean, standard deviation and statistical significance of the difference between the said parameters (see Table 6).

TABLE 6

Variation in the analytical parameters between the selection examination and the final examination.

| LABORATORY TESTS | SELECTION Mean ± SD | FINAL EXAM. Mean ± SD | Statistical significance |
|---|---|---|---|
| Haematology | | | |
| Erythrocytes ($10^{12}$/l) | 4.75 ± 0.46 | 4.79 ± 0.59 | n.s.s. |
| Haemoglobin (g/dl) | 13.7 ± 1.4 | 13.8 ± 1.6 | n.s.s. |
| Hematocrit (%) | 43.0 ± 4.2 | 43.0 ± 5.2 | n.s.s. |
| MCV (fl) | 90.6 ± 4.0 | 89.8 ± 4.2 | 0.001* |
| MCH (pg) | 28.9 ± 1.6 | 28.9 ± 1.7 | n.s.s.* |
| MCHC (g/dl) | 31.9 ± 1.4 | 32.2 ± 1.1 | n.s.s.* |
| Platelets ($10^9$/l) | 238.9 ± 48.1 | 240.5 ± 44.3 | n.s.s. |
| Leukocytes ($10^9$/l) | 6.3 ± 1.1 | 5.8 ± 1.3 | 0.038 |
| Neutrophils (%) | 59.6 ± 8.0 | 56.1 ± 7.4 | n.s.s. |
| Lymphocytes (%) | 30.0 ± 6.5 | 32.8 ± 6.2 | 0.010 |
| Monocytes (%) | 7.5 ± 1.7 | 7.8 ± 1.6 | n.s.s. |
| Eosinophils (%) | 2.3 ± 1.2 | 2.5 ± 1.2 | n.s.s. |
| Basophils (%) | 0.6 ± 0.5 | 0.7 ± 0.4 | n.s.s. |
| Blood chemistry | | | |
| Glucose (mg/dl) | 87.4 ± 6.4 | 85.2 ± 7.5 | n.s.s. |
| Total bilirubin (mg/dl) | 0.7 ± 0.2 | 0.7 ± 0.2 | n.s.s. |
| GOT-AST (UI/l) | 12.9 ± 3.5 | 12.5 ± 3.2 | n.s.s. |
| GPT-ALT (UI/l) | 11.1 ± 5.0 | 11.9 ± 6.6 | n.s.s.* |
| Alkaline phosphatase (UI/l) | 39.8 ± 10.2 | 39.0 ± 9.2 | n.s.s. |
| GGT (UI/l) | 10.8 ± 4.9 | 9.7 ± 4.3 | 0.001* |
| Creatinine (mg/dl) | 0.9 ± 0.2 | 0.9 ± 0.2 | n.s.s. |
| Urinalysis | | | |
| Density | 1.021 ± 0.008 | 1.023 ± 0.008 | n.s.s.* |
| pH | 6.3 ± 0.7 | 6.3 ± 0.6 | n.s.s.* | n.s.s.: Not statistically significant.
*Wilcoxon Test.

Differences were observed in some parameters between the selection examination and the final examination, however all the values were considered to be normal, with no clinical significance.

As indicated above, during the study, the vital signs (blood pressure and heart rate) were taken during the selection, and at different times during the treatment phase and in the final examination (see Tables 7 and 8).

The mean values for reach of the measurement times and the statistical analysis with a repeated measures ANOVA on the six volunteers taking part in period 1, is shown below (see Table 7).

TABLE 7

Vital signs during period 1 of the trial. n = 6.

| SBP (mm Hg) | Mean ± SD | p (comp. to selection) |
|---|---|---|
| SBP Selection | 116.8 ± 10.3 | — |
| SBP Baseline D 1 | 105.7 ± 6.8 | 0.008 |
| SBP 1 h | 107.7 ± 10.5 | 0.003 |
| SBP 4 h | 108.8 ± 11.6 | n.s.s. |
| SBP Final exam. | 112.0 ± 10.6 | n.s.s. |
| DBP (mm Hg) | | |
| DBP Selection | 61.5 ± 8.7 | — |
| DBP Baseline D 1 | 57.3 ± 10.5 | n.s.s. |
| DBP 1 h | 55.8 ± 9.6 | 0.011 |
| DBP 4 h | 57.3 ± 11.6 | n.s.s. |
| DBP Final exam. | 59.2 ± 7.2 | n.s.s. |
| HR (b.p.m.) | | |
| HR Selection | 69.7 ± 6.0 | — |
| HR Baseline D 1 | 58.0 ± 5.4 | 0.013 |
| HR 1 h | 58.7 ± 6.0 | 0.003 |
| HR 4 h | 55.5 ± 4.1 | 0.006 |
| HR Final exam. | 59.7 ± 2.6 | 0.003 |
| RR (r.p.m.) | | |
| RR Selection | 16.0 ± 2.8 | — |
| RR Baseline D 1 | 14.3 ± 1.5 | n.s.s. |
| RR Final exam. | 14.0 ± 2.6 | n.s.s. |
| T (° C .) | | |
| T Selection | 36.2 ± 0.3 | — |
| T Baseline D 1 | 36.1 ± 0.5 | n.s.s. |
| T Final exam. | 36.1 ± 0.3 | n.s.s. | n.s.s.: not statistically significant

The vital signs in period 2 were taken in the examination made on day 1 and on the one made on day 7, before and one hour after administration of the first and last dose of the investigational medicinal product. The vital signs were also taken during the selection examination and at the final examination. Taking the selection values as the baseline, the evolution of the vital signs was evaluated for the 24 volunteers for the course of the study, during period 2, using a repeated measures ANOVA (see Table 8).

TABLE 8

Vital signs during the second period of the trial. n = 24.

| SBP (mm Hg) | Mean ± SD | p (comp. to the Selection) |
|---|---|---|
| SBP Selection | 123.2 ± 9.5 | — |
| SBP Baseline D 1 | 118.0 ± 9.0 | 0.014 |
| SBP 1 h D 1 | 118.6 ± 7.5 | 0.040 |
| SBP Baseline D 7 | 119.0 ± 8.8 | 0.042 |
| SBP 1 h D 7 | 118.1 ± 7.2 | 0.017 |
| SBP Final exam. | 119.0 ± 7.5 | 0.016 |
| DBP (mm Hg) | | |
| DBP Selection | 65.5 ± 7.2 | — |
| DBP Baseline D 1 | 60.6 ± 6.6 | <0.001 |
| DBP 1 h D 1 | 60.6 ± 6.1 | <0.001 |
| DBP Baseline D 7 | 64.4 ± 6.7 | n.s.s. |
| DBP 1 h D 7 | 66.5 ± 8.0 | n.s.s. |
| DBP Final exam. | 60.5 ± 5.7 | 0.003 |
| HR (b.p.m.) | | |
| HR Selection | 69.4 ± 7.9 | — |
| HR Baseline D 1 | 64.9 ± 8.8 | 0.019 |
| HR 1 h D 1 | 63.2 ± 8.2 | 0.002 |
| HR Baseline D 7 | 66.1 ± 8.6 | 0.041 |
| HR 1 h D 7 | 60.8 ± 7.1 | <0.001 |
| HR Final exam. | 66.0 ± 8.3 | n.s.s. |
| RR (r.p.m.) | | |
| RR Selection | 16.0 ± 2.9 | — |
| RR Baseline D 1 | 14.8 ± 3.3 | n.s.s. |
| RR Baseline D 7 | 16.5 ± 3.6 | n.s.s. |
| RR Final exam. | 15.1 ± 3.0 | n.s.s. |
| T (° C.) | | |
| T Selection | 36.1 ± 0.4 | — |
| T Baseline D 1 | 35.9 ± 0.4 | n.s.s. |
| T Baseline D 7 | 35.9 ± 0.8 | n.s.s. |
| T Final exam. | 35.9 ± 0.5 | n.s.s. | n.s.s.: not statistically significant

An electrocardiogram was performed in the selection examination and a further electrocardiogram at the final examination. A comparison is made between the selection and final examinations, using a Student's t test for related samples. The following table summarises the mean and standard deviation for each parameter and the result of the analysis (see Table 9).

TABLE 9

Electrocardiogram: A comparison between the selection and final examinations

| | SELECTION-FINAL EXAM. | | |
|---|---|---|---|
| n = 30 | Selection (Mean ± SD) | Final exam. (Mean ± SD) | Statistical significance (p) |
| HR (b.p.m.) | 66.9 ± 9.0 | 61.1 ± 7.8 | <0.001 |
| RR (sec) | 148.2 ± 18.0 | 149.8 ± 15.7 | n.s.s.* |
| QRS (sec) | 87.7 ± 13.3 | 88.6 ± 13.8 | n.s.s. |
| QT (sec) | 369.9 ± 19.0 | 380.2 ± 25.5 | 0.003 |
| QTc (sec) | 388.5 ± 21.9 | 381.2 ± 18.1 | 0.014 | n.s.s.: not statistically significant.
*Wilcoxon Test

Statistically significant changes were observed in some of the blood pressure measurements in Table 7 and 8 and some of the heart rate measurements in Table 9, although all the values came within normal limits, and therefore these differences are not clinically significant.

Systemic tolerance was good, with no alterations in blood and urine analyses, electrocardiogram or in the examination made during the final assessment.

Blood analysis was performed to determine SEQ ID NO: 2 concentrations in plasma samples obtained following the administration of the drug. During the first period, sampling was performed over the 4 hours following administration, with blood being extracted at 5, 15, 30 minutes and 4 hours after product administration. During the second period blood samples were collected 5 minutes after administration on day 1, and again on day 7 both before compound administration and also 5 minutes after product administration.

A pharmacokinetic profile could not be determined for either period, as the compound was not detected in any of the collected blood samples with the validated bioanalytical method (LLOQ: 10 ng/mL). The absence of detectable amounts of compound in blood is in line with expected rapid degradation of RNA upon entering the bloodstream due to presence of RNAses.

All these facts support the conclusion that SEQ ID NO: 2 shows good tolerance in an ophthalmic solution in healthy humans.

Given the positive results obtained in animal models and the absence of toxicity in healthy humans the compounds are then tested in patients suffering from ocular pain and dry eye.

Subjects

Sixty adult patients who were diagnosed with mild to moderate ocular pain and dry eye syndrome are recruited. Of these, half of them are over 65 years of age. Levels of ocular disease are established using OSDI© (ocular surface disease index) questionnaire developed by Allergan Inc. and VAS (visual analogue scale) evaluation. Inclusion criteria were a score of 13-30 in OSDI© for dry eye and a score of 2 to 7 VAS for pain. A comprehensive physical examination and an ocular examination are performed before admittance into the study to assure the suitability of the subjects for participation in the study.

Study Design

A parallel, placebo controlled, double-masked clinical study was designed to evaluate the analgesic effect and tolerability of the compound of SEQ ID NO: 2 administered daily as eye drops during 10 days of treatment.

Secondary objectives being assessment of local tolerability after each dose, systemic tolerability (effect on laboratory parameters, physical examination, and vital signs), and changes (if any) in visual acuity, intraocular pressure, Schirmer's test and tear break-up time, possibly related to the investigational product.

In all cases, the drug or placebo is instilled in both eyes. Both eyes are monitored in a blinded fashion.

Baseline Period

Up to 15 days before the first administration of the investigational product subjects are enrolled for eligibility to participate in the Treatment Period of the clinical trial.

Treatment Period

On Day 1 subjects are randomised to compound or placebo in a ratio of 2:1 administered in topically to the eye, as eye drops. Subjects receive a final volume of 40 of compound or vehicle (placebo) per eye. The dose administered is 900 µg of compound per eye.

Subjects return each day (including bank holidays and weekends) to the site for investigational product administration and assessments. Subjects receive 1 dose of the compound once a day in both eyes for 10 days.

On day 10 patients again receive a thorough examination equivalent to that performed at baseline.

Follow-Up Visit

The final assessment is done at the follow-up visit which takes place 14 to 20 days after the first administration (from 4 to 10 days after the last administration) to determine patients' evolution after finalisation of the treatment period.

To determine the effect of SEQ ID NO: 2 on patients' level of dry eye and ocular pain, each individual score on OSDI© and VAS is taken down the day before beginning treatment, and compared to that of day 10. The result is measured specifically in changes in median score resulting from OSDI© questionnaire, and changes in median intensity of VAS evaluation.

Also, results from ocular explorations performed before initiating treatment and after 10 days are compared to confirm tolerability.

Results

The OSDI© questionnaire is assessed on a scale of 0 to 100, with higher scores representing greater disability. The index demonstrates sensitivity and specificity in distinguishing between normal subjects and patients with dry eye disease. The OSDI© consists of twelve questions and is designed to provide a quick indication of the symptoms that are consistent with dry eye disease. The OSDI© is a valid and reliable instrument for measuring the severity of dry eye disease (normal, mild to moderate, and severe) and has been accepted by the Food and Drug Administration for use in clinical trials. The validity and reliability of the OSDI© have been assessed and it has been found to provide good to excellent reliability, validity, sensitivity and specificity for dry eyes. An estimate overall OSDI© score defined the ocular surface as normal (0-12 points) or as having mild (13-22 points), moderate (23-32 points), or severe (33-100 points) disease.

TABLE 10

OSDI © for dry eye. n = 23. V0 corresponds to the OSDI © the day before beginning the treatment, and VD10 corresponds to the OSDI © the day 10. The result and % shows the changes in median score on patients' level of dry eye.

| No | V0 | VD10 | RESULT | % |
|---|---|---|---|---|
| 1 | 20.45 | 6.82 | From mild to normal | −66.65 |
| 2 | 27.08 | 20.83 | From moderate to mild | −23.08 |
| 3 | 38.64 | 50 | From less severe to more severe | 29.40 |
| 4 | 40.91 | 11.36 | From severe to normal | −72.23 |
| 5 | 37.5 | 33.33 | From more severe to less severe | −11.12 |
| 6 | 52.08 | 10.42 | From severe to normal | −79.99 |
| 7 | 34.09 | 9.09 | From severe to normal | −73.34 |
| 8 | 60 | 17.5 | From severe to mild | −70.83 |
| 9 | 43.18 | 25 | From severe to moderate | −42.10 |
| 10 | 50 | 56.81 | From less severe to more severe | 13.62 |
| 11 | 32.5 | 10.4 | From moderate to normal | −68.00 |
| 12 | 39.58 | 29.16 | From severe to moderate | −26.33 |
| 13 | 43.75 | 36.36 | From more severe to less severe | −16.89 |
| 14 | 43.75 | 59.09 | From less severe to more severe | 35.06 |
| 15 | 43.18 | 52.7 | From less severe to more severe | 22.05 |
| 16 | 45.45 | 43.18 | From more severe to less severe | −4.99 |
| 17 | 25 | 15.9 | From moderate to mild | −36.40 |
| 18 | 63.63 | 45.45 | From more severe to less severe | −28.57 |
| 19 | 43.75 | 45.83 | From less severe to more severe | 4.75 |
| 20 | 52.7 | 47.72 | From more severe to less severe | −9.45 |
| 21 | 50 | 55 | From less severe to more severe | 10.00 |
| 22 | 29.16 | 10.4 | From moderate to normal | −64.33 |
| 23 | 54.16 | 45.45 | From more severe to less severe | −16.08 |

The pain questionary VAS is a unidimensional measure of pain intensity, which has been widely used in diverse adult populations. The VAS measures pain that ranges across a continuum of values and cannot easily be directly measured, like the ocular pain. For pain intensity in the VAS, the scale is most commonly anchored by "no pain" (score of 0) and "worst imaginable pain" (score of 10).

TABLE 11

VAS for ocular pain. n = 23. V0 corresponds to the VAS the day before beginning the treatment, and VD10 corresponds to the VAS the day 10. The % shows the changes in median score on patients' level of ocular pain on the right and left eye.

| No | EYE | V0 | VD10 | % |
|---|---|---|---|---|
| 1 | Right eye | 24 | 2 | −91.67 |
|   | Left eye | 30 | 2 | −93.33 |
| 2 | Right eye | 38 | 13 | −65.79 |
|   | Left eye | 50 | 10 | −80.00 |
| 3 | Right eye | 40 | 33 | −17.50 |
|   | Left eye | 30 | 20 | −33.33 |
| 4 | Right eye | 20 | 4 | −80.00 |
|   | Left eye | 20 | 5 | −75.00 |
| 5 | Right eye | 60 | 60 | 0.00 |
|   | Left eye | 70 | 70 | 0.00 |
| 6 | Right eye | 50 | 40 | −20.00 |
|   | Left eye | 70 | 40 | −42.86 |
| 7 | Right eye | 53 | 37.5 | −29.25 |
|   | Left eye | 67 | 46.5 | −30.60 |
| 8 | Right eye | 70 | 42 | −40.00 |
|   | Left eye | 70 | 46 | −34.29 |
| 9 | Right eye | 7 | 5.5 | −21.43 |
|   | Left eye | 5 | 4.5 | −10.00 |

TABLE 11-continued

VAS for ocular pain. n = 23. V0 corresponds to the VAS the day before beginning the treatment, and VD10 corresponds to the VAS the day 10. The % shows the changes in median score on patients' level of ocular pain on the right and left eye.

| No | EYE | V0 | VD10 | % |
|---|---|---|---|---|
| 10 | Right eye | 3.5 | 0.5 | −85.71 |
|    | Left eye  | 3.5 | 1.1 | −68.57 |
| 11 | Right eye | 5   | 2   | −60.00 |
|    | Left eye  | 4   | 1.1 | −72.50 |
| 12 | Right eye | 5   | 6.4 | 28.00 |
|    | Left eye  | 4   | 3.3 | −17.50 |
| 13 | Right eye | 7   | 6   | −14.29 |
|    | Left eye  | 7   | 6.5 | −7.14 |
| 14 | Right eye | 4   | 6.8 | 70.00 |
|    | Left eye  | 5   | 6.8 | 36.00 |
| 15 | Right eye | 7   | 8   | 14.29 |
|    | Left eye  | 7   | 7   | 0.00 |
| 16 | Right eye | 7   | 6   | −14.29 |
|    | Left eye  | 4   | 7   | 75.00 |
| 17 | Right eye | 3.7 | 2.5 | −32.43 |
|    | Left eye  | 6   | 2   | −66.67 |
| 18 | Right eye | 7   | 4   | −42.86 |
|    | Left eye  | 6   | 5   | −16.67 |
| 19 | Right eye | 4.9 | 5.7 | 16.33 |
|    | Left eye  | 5.5 | 5.5 | 0.00 |
| 20 | Right eye | 3   | 7   | 133.33 |
|    | Left eye  | 7   | 3   | −57.14 |
| 21 | Right eye | 2   | 4.4 | 120.00 |
|    | Left eye  | 7   | 6.7 | −4.29 |
| 22 | Right eye | 2   | 2.4 | 20.00 |
|    | Left eye  | 2   | 1.3 | −35.00 |
| 23 | Right eye | 6   | 3   | −50.00 |
|    | Left eye  | 7   | 5   | −28.57 |

CONCLUSIONS

Taking into account the ratio compound:placebo of 2:1 of the clinical trial, and that this ratio is maintained independently of the number of patients analysed, it can be concluded that the effect of SEQ ID NO: 2 applied daily to the patient, is able to reduce the severity of dry eye disease and reduce the ocular pain when administered topically to the eye.

REFERENCES

Baumann T K & Martenson M E. (2000). "Extracellular protons both increase the activity and reduce the conductance of capsaicin-gated channels." *J Neurosci* 20:RC80.

Caterina et al. (1997). "The capsaicin receptor: a heat-activated ion channel in the pain pathway." *Nature* 389(6653):816-24.

Caterina et al. (2001). "The vanilloid receptor: a molecular gateway to the pain pathway." *Annu Rev Neurosci*. 24:487-517.

Cerutti, L., N. Mian, et al. (2000). "Domains in gene silencing and cell differentiation proteins: the novel PAZ domain and redefinition of the Piwi domain." *Trends Biochem Sci* 25(10): 481-2.

Collins, R. E. and X. Cheng (2005). "Structural domains in RNAi." *FEBS Lett* 579(26): 5841-9.

Doench, J. G. Sharp, P. A. "specificity of microRNA target selection in translational repression" Genes Dev. 18, 504-511; 2004

Elbashir, S. M., W. Lendeckel, et al. (2001). "RNA interference is mediated by 21- and 22-nucleotide RNAs." *Genes Dev* 15(2): 188-200.

Fire, A., S. Xu, et al. (1998). "Potent and specific genetic interference by double-stranded RNA in *Caenorhabditis elegans*." *Nature* 391(6669): 806-11.

Gonzalez, G. G., Garcia, P. et al. (1993). "Reduction of capsacin-induced ocular pain and neurogenic inflammation by calcium antagonists." *Invest Ophthalmol Vis Sci* 34(12):3329-3335.

Hutvagner, G. and P. D. Zamore (2002). "A microRNA in a multiple-turnover RNAi enzyme complex." *Science* 297(5589): 2056-60.

Jia et al. (2005). "TRPV1 receptor: a target for the treatment of pain, cough, airway disease and urinary incontinence." *Drug News Perspect* 18(3):165-71.

Lewis, B. P., Shih I. Et al. "prediction of mammalian micro RNA targets" Cell 115:787-798; 2003

Liu, J., M. A. Carmell, et al. (2004). "Argonaute2 is the catalytic engine of mammalian RNAi." *Science* 305(5689): 1437-41.

Ma, J. B., Y. R. Yuan, et al. (2005). "Structural basis for 5'-end-specific recognition of guide RNA by the *A. fulgidus* Piwi protein." *Nature* 434(7033): 666-70.

Montell et al. (2002). "Short hairpin RNAs (shRNAs) induce sequence-specific silencing in mammalian cells." *Genes Dev* 16(8):948-58.

Nykanen, A., B. Haley, et al. (2001). "ATP requirements and small interfering RNA structure in the RNA interference pathway." *Cell* 107(3): 309-21.

Orban, T. I. and E. Izaurralde (2005). "Decay of mRNAs targeted by RISC requires XRN1, the Ski complex, and the exosome." *Rna* 11(4): 459-69.

Parrish, S., J. Fleenor, et al. (2000). "Functional anatomy of a dsRNA trigger: differential requirement for the two trigger strands in RNA interference." *Mol Cell* 6(5): 1077-87.

Rand, T. A., S. Petersen, et al. (2005). "Argonaute2 cleaves the anti-guide strand of siRNA during RISC activation." *Cell* 123(4): 621-9.

Reynolds, A., Leake, D., et al. (2004). "Rational siRNA design for RNA interference" *Nat Biotechnol* 22(3):326-30.

Schubert, S. et al. (2005). "Local RNA target structure influences siRNA efficacy: systematic analysis of intentionally designed binding regions." *J Mol Biol* 348:883-893.

Song, J. J., S. K. Smith, et al. (2004). "Crystal structure of Argonaute and its implications for RISC slicer activity." *Science* 305(5689): 1434-7.

Ui-Tei, K., Naito, Y., et al. (2004). "Guidelines for the selection of highly effective siRNA sequences for mammalian and chick RNA interference." *Nucleic Acids Res* 32(3): 936-48.

The invention claimed is:

1. A method of treating dry eye and/or ocular pain in a subject in need thereof, said method comprising administering topically to the eye of the subject an siRNA having the sequence as set forth in SEQ ID NO: 2 and targeted to SEQ ID NO: 1, said siRNA administered at a dosage of 0.3 mg to 0.9 mg per day; wherein the dosage is effective in reducing dry eye and/or ocular pain in the subject undergoing treatment.

2. The method according to claim 1, wherein the siRNA is administered for 5 to 15 days.

3. The method according to claim 1, wherein the siRNA is administered for 10 days.

4. The method according to claim 1, wherein the siRNA is administered chronically.

5. A unit dosage form for treating eye and/or ocular pain in a subject in need thereof, said dosage form comprising an siRNA having the sequence as set forth in SEQ ID NO: 2 and targeted to SEQ ID NO: 1 in a therapeutic amount of 0.3 mg to 0.9 mg, and a pharmaceutically acceptable carrier or diluent.

6. A kit for administering an siRNA having the sequence as set forth in SEQ ID NO: 2 and targeted to SEQ ID NO: 1, said kit comprising a dosage of the siRNA of 0.3 mg to 0.9 mg for daily administration, and printed instructions for administering the siRNA.

7. The method according to claim 1, wherein the siRNA is administered at a dosage of 0.5 mg per day.

8. The unit dosage form according to claim 5, wherein said unit dosage form comprises said siRNA in a therapeutic amount of 0.5 mg.

9. The kit according to claim 6, wherein said kit comprises said siRNA in a dosage of 0.5 mg.

10. The method according to claim 7, wherein the siRNA is administered for 5 to 15 days.

11. The method according to claim 7, wherein the siRNA is administered for 10 days.

12. The method according to claim 7, wherein the siRNA is administered chronically.

13. The method of claim 1 wherein the subject is human.

14. The method of claim 7 wherein the subject is human.

* * * * *